United States Patent
Ungeprapakorn et al.

(10) Patent No.: US 12,405,272 B2
(45) Date of Patent: Sep. 2, 2025

(54) ASSAY DEVICE

(71) Applicant: SPD Swiss Precision Diagnostics GMBH, Geneva (CH)

(72) Inventors: Catherine Ungeprapakorn, Geneva (CH); Stephen Carlisle, Geneva (CH); Balbir Raj, Geneva (CH)

(73) Assignee: SPD Swiss Precision Diagnostics GMBH, Geneva (CH)

( * ) Notice: Subject to any disclaimer, the term of this patent is extended or adjusted under 35 U.S.C. 154(b) by 905 days.

(21) Appl. No.: 17/602,592

(22) PCT Filed: Apr. 9, 2020

(86) PCT No.: PCT/EP2020/060155
§ 371 (c)(1),
(2) Date: Oct. 8, 2021

(87) PCT Pub. No.: WO2020/208141
PCT Pub. Date: Oct. 15, 2020

(65) Prior Publication Data
US 2022/0187325 A1    Jun. 16, 2022

(30) Foreign Application Priority Data

Apr. 10, 2019   (GB) ..................................... 1905090

(51) Int. Cl.
*G01N 33/543*   (2006.01)
*G01N 33/76*    (2006.01)

(52) U.S. Cl.
CPC . *G01N 33/54388* (2021.08); *G01N 33/54387* (2021.08); *G01N 33/76* (2013.01); *G01N 2333/59* (2013.01)

(58) Field of Classification Search
CPC ....... G01N 33/54388; G01N 33/54387; G01N 33/76; G01N 233/59
See application file for complete search history.

(56) References Cited

U.S. PATENT DOCUMENTS

| 4,806,312 | A  | 2/1989 | Greenquist |
| 7,090,194 | B2 | 8/2006 | Sampson    |

(Continued)

FOREIGN PATENT DOCUMENTS

| CN | 108226460 A  | 6/2018 |
| DE | 10337772 A1  | 3/2005 |

(Continued)

OTHER PUBLICATIONS

International Search Report and Written Opinion for International Application No. PCT/EP2020/060155 dated May 25, 2020.

(Continued)

*Primary Examiner* — Jill A Warden
*Assistant Examiner* — Alex Ramirez
(74) *Attorney, Agent, or Firm* — Foley Hoag LLP; Erik A. Huestis

(57) ABSTRACT

The present invention provides assay devices and methods for detecting the presence of an analyte in a sample. Devices according to the invention include a reagent zone, one or more capture zones and a detection zone. Capture zones can reduce the quantity of labelled conjugate that reaches the detection zone in the presence of a negative marker in the sample and/or in the absence of a positive marker in the sample, facilitating high sensitivity and improved specificity testing.

25 Claims, 12 Drawing Sheets

(56) References Cited

U.S. PATENT DOCUMENTS

Figure 1A:
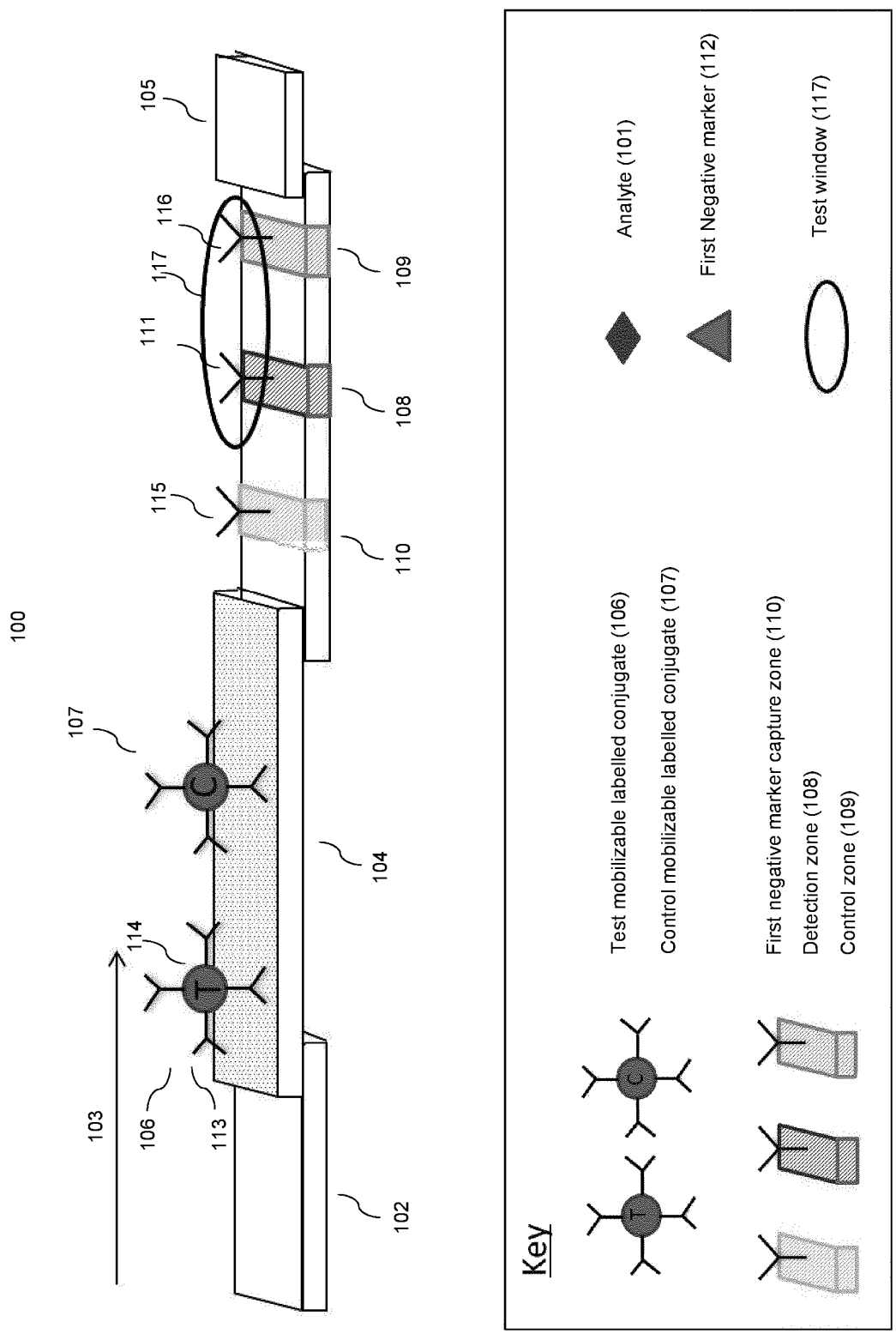

| | | |
|---|---|---|
| 7,465,587 B2 | 12/2008 | Imrich |
| 8,101,369 B2 | 1/2012 | Nam et al. |
| 2002/0142291 A1 | 10/2002 | Bauer et al. |
| 2006/0121626 A1 | 6/2006 | Imrich |
| 2006/0246435 A1 | 11/2006 | Kempin et al. |
| 2008/0118911 A1 | 5/2008 | Hermann et al. |
| 2009/0208983 A1 | 8/2009 | Nam et al. |
| 2011/0143335 A1 | 6/2011 | Johnson et al. |
| 2011/0151432 A1 | 6/2011 | Zappia et al. |
| 2017/0234866 A1 | 8/2017 | Hamad-Schifferli et al. |
| 2019/0204334 A1* | 7/2019 | McCarthy ............ G01N 33/743 |

FOREIGN PATENT DOCUMENTS

| | | |
|---|---|---|
| EP | 1240517 B1 | 8/2004 |
| EP | 1485717 B1 | 2/2007 |
| EP | 1075661 B1 | 8/2007 |
| EP | 2137532 B1 | 8/2015 |
| WO | WO-1993/003175 A1 | 2/1993 |
| WO | WO-1997/031269 A1 | 8/1997 |
| WO | WO-1999/060402 A1 | 11/1999 |
| WO | WO-2001/042788 A2 | 6/2001 |
| WO | WO-2005/059547 A2 | 6/2005 |
| WO | WO-2015/049508 A1 | 4/2015 |
| WO | WO-2016/156981 A1 | 10/2016 |
| WO | WO-2017/138946 A1 | 8/2017 |
| WO | WO-2020/208141 A1 | 10/2020 |

OTHER PUBLICATIONS

Search Report for United Kingdom Application No. GB1905090.5 dated Jan. 10, 2020.

* cited by examiner

ASSAY DEVICE

RELATED APPLICATIONS

This application is a U.S. National Phase of International Application No. PCT/EP2020/060155, filed Sep. 4, 2020, which claims the benefit of GB 1905090.5, filed Oct. 4, 2019, which are hereby incorporated by reference herein in their entirety.

FIELD OF THE INVENTION

The invention provides an assay device for detecting the presence of an analyte in a sample.

BACKGROUND

Simple lateral flow immunoassay devices have been developed and commercialised for detection of analytes in fluid samples, see for example EP291194. Such devices typically comprise a porous carrier comprising a dried, mobilisable labelled binding reagent capable of binding to the analyte in question, and an immobilised binding reagent also capable of binding to the analyte provided at a detection zone downstream from the labelled binding reagent. The mobilisable labelled binding reagent is mobile within the porous carrier when in the moist state. The immobilised binding reagent is permanently immobilised in the detection zone and is therefore not mobile in the moist state. Detection of labelled binding reagent captured at the detection zone provides an indication of the presence of analyte in the sample.

Alternatively, when the analyte of interest is a hapten, the immunoassay device may employ a competition reaction wherein a labelled analyte or analyte analogue competes with analyte present in the sample for binding to an immobilised binding reagent at a detection zone. Alternatively the assay device may employ an inhibition reaction whereby an immobilised analyte or analyte analogue is provided at a detection zone, the assay device also comprising a mobilisable labelled binding reagent for the analyte.

An assay device may be able to detect the presence and/or amount of more than one analyte. For example, in the case of assays detecting the presence of drugs of abuse, the device may be capable of determining a whole panel of drugs. Such lateral flow immunoassay devices are generally provided with multiple detection zones, such zones being provided on a single or multiple lateral flow carriers, within the assay device.

Digital devices have been developed comprising an optical detection means arranged to determine the result of the assay as well as a display means to display the result of the assay. Digital assay readers for use in combination with assay test-strips for determining the concentration and/or amount of analyte in a fluid sample are known as are assay devices comprising an integral digital assay reader. An example of such a device is disclosed in EP1484601.

Light from a light source, such as a light emitting diode (LED), is shone onto a portion of the porous carrier and either reflected or transmitted light is detected by a photodetector. Typically, the reader will have more than one LED to illuminate various zones of the carrier, and a corresponding photodetector is provided for each of the plurality of LEDs. EP1484601 discloses an optical arrangement for a lateral flow test strip digital reading device comprising a baffle arrangement allowing for the possibility of reducing the number of photodetectors in the device.

Assay technology of the foregoing type has been implemented into "self-test" pregnancy testing devices. These are, typically, devices which are used by women who suspect they may be pregnant. As such, they must be designed in such a way that they are easy to use (not requiring any medical or technical training), and are typically disposable after a single use. The device is usually a lateral flow immunoassay device, and normally the test is initiated by contacting a sampling portion of a lateral flow assay stick with a urine sample. The sampling portion of the assay stick may be immersed into a sample of urine in a container or, more typically, the user may urinate directly onto the sampling portion. The assay then runs without the user needing to perform any further steps, and the result is indicated and read by eye or, in a digital device, is determined by an assay result reading means and displayed to the user, by means of a display such as, for example, a liquid crystal display (LCD).

Conventional pregnancy tests of this sort work by measuring human chorionic gonadotrophin (hCG), in the sample. The hCG is produced by the developing embryo and a concentration of hCG in the sample above a certain threshold will trigger a positive (i.e. "pregnant") result.

There is a need for an improved pregnancy test, especially an improved self-test pregnancy test: many women wish to know, as soon as possible, if they are pregnant. Early confirmation of pregnancy is beneficial, as a positive pregnancy test can elicit important positive behavioural changes that promote maternal and fetal wellbeing. For example, prompting pregnant women to modify their diet, begin taking pregnancy supplements and avoid risks to the developing foetus including use of pharmaceuticals, alcohol and occupational exposure to mutagens/teratogens. A recent study by, Prior et al (Obstetrics and Gynaecology, 2017, 129 (4), 727-733) examined the alcohol consumption of 5036 pregnant women and found that over half of women reported some use of alcohol while trying to conceive, but the majority stopped drinking, or at least reduced their alcohol consumption, on obtaining a positive pregnancy test. They concluded that promoting early pregnancy awareness was more effective than promoting abstinence from alcohol among all who could conceive and this is likely to apply to other important health messages relating to behavior in pregnancy.

This has resulted in a drive towards tests with high sensitivity, which can detect hCG in the early stages of pregnancy in samples, such as urine, at very low concentration. However, the use of high sensitivity tests measuring hCG creates a problem because hCG can sometimes be present in urine, at relatively low concentration, for reasons other than pregnancy, such that a very sensitive pregnancy test may give a false positive result. For example hCG may be produced, at low levels, in the pituitary gland of women who are peri-menopausal and menopausal.

According to the World Health Organization, the recognized definitions of "menopause" and "peri-menopause" are as follows:

Menopause (natural menopause)—is defined as the permanent cessation of menstruation resulting from the loss of ovarian follicular activity. Natural menopause is recognized to have occurred after 12 consecutive months of amenorrhea, for which there is no other obvious pathological or physiological cause. Menopause occurs with the final menstrual period (FMP) which is known with certainty only in retrospect a year or more after the event.

Peri-menopause—the term perimenopause includes the period immediately prior to the menopause (when the endocrinological, biological, and clinical features of approaching menopause commence) and the first year after menopause.

Accordingly, for present purposes, peri-menopausal women are defined as being those women who are in peri-menopause according to the WHO definition above and post-menopausal women are defined as those who have undergone menopause according to the WHO definition above.

In the USA and across much of the developed world, women are waiting longer to start a family. Between 2000 and 2014 the mean age of first time mothers in the USA increased by 1.4 years from 24.9 to 26.3 (Mathews and Hamilton, National Center for Health Statistics, Data Brief 2016; No 232) and between 2000 and 2012 first birth rates for women aged 35-39 and 40-44 increased by 24% and 35% respectively (Mathews and Hamilton, National Center for Health Statistics, Data Brief 2014; No 152). More recently, data from the U.S. Department of Health and Human Services for the year 2017 (Brady et al, National Center for Health Statistics. Report No 004. May 2018), shows birth rates have declined for nearly all age groups of women under 40, but rose for women in their early 40s. The provisional birth rate for women aged 40-44 in 2017 was 11.6 births per 1,000 women, up 2% from 2016. The rate for this age group has generally risen since 1982. According to one study, up to 10% of the sales of OTC pregnancy tests have been to women>40 yrs old (Leavitt SA 2006, "A private little revolution: the home pregnancy test in American Culture". Bulletin of the History of Medicine 2006 80, 317-45).

Peri-menopause, which may last up to 10 years can begin in a woman's thirties (American College of Obstetricians and Gynecologists 2015, FAQ047), causes shifts in hormone levels and may affect ovulation causing irregular menstrual cycles. Menopause, on average occurs at age 51, but before the age of 40 in 1% of women (Haller-Kikkatalo et al, Human Reproduction 2015 30 (5), 1229-1238). Many women have poor understanding of their fertility and will be unaware that they are experiencing peri-/post-menopause. The disruption to a woman's menstrual cycle in peri-menopause, or their absence in menopause, could be mistaken for a missed period and prompt her to test for pregnancy.

Elevated levels of hCG in peri-menopause have been reported in published literature, with Snyder et al., (Clinical Chemistry 2005 51, 1830-1835) finding 1.3% of the population they examined having serum hCG levels greater than 5 mIU/ml.

In menopause, the production of pituitary hCG has been shown to increase (Odell and Griffin, New England Journal of Medicine 1987 317, 1688-91), (Stenman et al, Journal of Clinical Endocrinology & Metabolism 1987 64, 730-6). As women approach menopause and the number of ovarian follicles available for recruitment each cycle falls, more follicle stimulating hormone (FSH) is required in order to stimulate the remaining follicles. As a result, FSH levels rise and this elevated FSH may also persist in menopause for some women. The increase in FSH production in peri- and post-menopausal women can result in co-production of small amounts of hCG which is produced in the pituitary gland.

The production of hCG in post-menopausal women has been documented by several researchers e.g. Snyder et al., (Clinical Chemistry 2005 51, 1830-1835) and Alfthan et al (Clinical Chemistry 1992 38, 1981-1987) and serum levels as high as 13 mIU/ml have been reported, with 6.7% of women having a hCG concentration greater than 5 mIU/ml (Snyder et al, 2005).

To detect pregnancy as early as six days before the missed period, a high sensitivity hCG assay is required. However, the risk with a highly sensitive pregnancy test that detects low levels of hCG only, (i.e. one that indiscriminately detects both pregnancy and pituitary derived hCG), is that it is also more likely to detect low levels of pituitary hCG and therefore, give a false positive result.

In a different context, in many countries, tests for serum hCG are routinely performed on nearly all women patients of child-bearing age before conducting any medical intervention which might harm a developing fetus. The problem of elevated serum hCG levels, due to "pituitary" hCG, in peri- and post-menopausal women is recognized. Snyder et al., (Clinical Chemistry 2005 51, 1830-1835) examined changes with age in serum hCG concentrations of non-pregnant women and investigated the use of serum FSH measurements as an aid to interpreting higher than expected hCG results. They suggested that a combination of serum hCG measurements, knowledge of the age of the subject, and serum FSH measurements, could be used to reduce or avoid "false positive" pregnancy results. These workers were not, however, concerned with self-test pregnancy tests and, in particular, were not concerned with detecting pregnancy at a very early stage.

Attempts have been made to reduce the occurrence of false positive pregnancy results caused by the detection of non-pregnancy associated hCG present in urine samples. For example, WO 2016156981 discloses a test device to detect pregnancy comprising: an assay means to measure the absolute or relative amount of hCG in a sample from the subject; an assay means to measure the absolute or relative amount of FSH in a sample from the subject; and an assay means to measure the absolute or relative amount of one or more progesterone metabolites, in a sample from the subject. The concept is based on the following observations. Firstly, following conception, further ovulatory cycles are unnecessary since the woman is already pregnant. Accordingly, after conception, folliculargenesis is inhibited by suppression of FSH production. Thus, in a pregnant woman, one would expect to observe elevated levels of hCG and low levels of FSH. Secondly, during the first 10-12 weeks of pregnancy, progesterone produced by the corpus luteum supports the endometrium, thus allowing the pregnancy to continue. Progesterone is raised during parts of the luteal phase of menstrual cycles, but this level falls back to baseline levels if pregnancy does not occur (i.e. if the subject menstruates). However, if pregnancy occurs, the levels of progesterone (and its urinary metabolites) will remain elevated and will continue to rise through pregnancy, so that progesterone (and its urinary metabolites) can be used as an adjunct to hCG as an additional confirmation of pregnancy. Thus, WO 2016156981 seeks to address the issue of false positive pregnancy results by proposing a test device that includes, in addition to an assay for hCG, an assay to measure FSH and an assay to measure one or more progesterone metabolites. The results of the FSH and progesterone metabolite assays are used to decide whether an indication of pregnancy can be given based on a positive hCG result.

The reading and interpretation of numerous assay results to decide whether a positive result can be declared is laborious and leaves room for error, particularly for typical users of such devices, who are not trained in carrying out or interpreting biochemical assays. WO 2016156981 proposes the use of digital assay readers to reduce the burden on the user. However, a drawback of this approach is that it adds to the cost and complexity of the test device.

SUMMARY OF THE INVENTION

The invention provides an assay device for detecting the presence of an analyte in a sample, the device comprising an assay flow path, the flow path comprising:
(a) a reagent zone comprising a mobilisable labelled conjugate configured for association with the analyte, wherein the mobilisable labelled conjugate is also
  i. configured for association with a first negative marker and/or
  ii. configured for association with a positive marker, and/or
  iii. comprises a positive marker or positive marker conjugate or is configured for association with a positive marker or positive marker conjugate such that the positive marker or positive marker portion of the conjugate is accessible for binding,
(b) one or more capture zones comprising immobilised capture species for capturing the labelled conjugate when the sample contains negative marker and/or immobilised capture species for capturing labelled conjugate when the sample does not contain positive marker,
(c) a detection zone for capturing labelled conjugate when the sample contains analyte and has not been captured by a capture zone,
wherein the one or more capture zones are downstream of the reagent zone and the detection zone is downstream of the one or more capture zones.

Where the reagent zone comprises option (ii) and option (iii), the positive marker of option (ii) may be different to the positive marker or positive marker portion of the positive marker conjugate of option (iii).

Also provided is an assay device for detecting the presence of an analyte in a sample, the device comprising an assay flow path, the flow path comprising:
(a) a reagent zone comprising a mobilisable labelled conjugate comprising a detectable label directly or indirectly linked to
  (i) means for associating the labelled conjugate with the analyte and means for associating the labelled conjugate with a first negative marker which may be present in the sample, and/or
  (ii) means for associating the labelled conjugate with the analyte, wherein the labelled conjugate further comprises a positive marker or positive marker conjugate a positive marker portion of which is accessible for binding and/or wherein a mobilisable positive marker or positive marker conjugate is provided separately in the reagent zone and is configured to associate with the labelled conjugate following mobilisation such that, when the labelled conjugate is associated with the positive marker or positive marker conjugate, the positive marker or positive marker portion of the conjugate is accessible for binding, and/or
  (iii) means for associating the labelled conjugate with the analyte and means for associating the labelled conjugate with a positive marker, which may be present in the sample, or a positive marker or positive marker conjugate of the device, and optionally wherein the reagent zone further comprises a mobilisable positive marker or positive marker conjugate for immobilisation downstream of the reagent zone, (b) one or more capture zones, wherein
  (i) if the reagent zone comprises option (i),
    at least one capture zone comprises an immobilised capture species configured to capture a complex comprising the labelled conjugate and the first negative marker wherein capture of the complex is preferably achieved by a specific binding reaction with first negative marker,
  (ii) if the reagent zone comprises option (ii),
    at least one capture zone comprises an immobilised capture species configured to capture positive marker when present in the sample or a labelled conjugate comprising or associated with the positive marker or positive marker conjugate, wherein capture of the labelled conjugate is preferably achieved by a specific binding reaction with positive marker or positive marker conjugate,
  (iii) if the reagent zone comprises option (iii),
    at least one capture zone comprises an immobilised capture species configured to capture labelled conjugate comprising means for associating the labelled conjugate with a positive marker or positive marker conjugate, wherein the immobilised capture species comprises or consists of an immobilised positive marker or positive marker conjugate, and/or if the reagent zone comprises a mobilisable positive marker or positive marker conjugate, the at least one capture zone comprises an immobilised capture species for locating the mobilisable positive marker or positive marker conjugate at the capture zone such that the positive marker or positive marker portion of the conjugate is accessible for binding, wherein capture of the labelled conjugate is preferably achieved by a specific binding reaction with the means for associating the labelled conjugate with a positive marker or positive marker conjugate,
(c) a detection zone comprising immobilised binding reagent for capturing a complex comprising the labelled conjugate and the analyte, wherein capture of the complex is preferably achieved by a specific binding reaction with the analyte,
wherein the or each capture zone is downstream of the reagent zone, and the detection zone is downstream of the or each capture zone.

Embodiments of the invention include assay devices that include, but are not limited to, the following combinations of reagent zone and capture zone options:

| Reagent zone option | Capture zone option |
| --- | --- |
| (i) | (i) |
| (i) and (ii) | (i) and (ii) |
| (i), (ii) and (iii) | (i), (ii) and (iii) |
| (i) and (iii) | (i) and (iii) |
| (ii) | (ii) |
| (ii) and (iii) | (ii) and (iii) |
| (iii) | (iii) |

Additional embodiments of the invention are set out in the dependent claims and the following description. In an embodiment, the assay device is adapted to reduce the quantity of labelled conjugate that reaches the detection zone in the presence of one or more additional negative markers. In an embodiment, the assay device is adapted to reduce the quantity of labelled conjugate that reaches the detection zone in the absence of one or more additional positive markers.

As discussed in further detail below, where an assay device of the invention includes immobilised capture species for reducing the quantity of labelled conjugate that reaches the detection zone in the presence of a first negative marker, the assay device may also include any suitable reagents and capture immobilised capture species disclosed herein for reducing the quantity of labelled conjugate that reaches the detection zone in the presence of a second negative marker. This concept can be extended to reduce the quantity of labelled conjugate that reaches the detection zone in the presence of further negative markers.

In embodiments in which reagent zone option (ii) and reagent zone option (iii) are present, preferably the positive marker of option (ii) is different to the positive marker of option (iii). For example, the positive marker of option (ii) may be a first positive marker, and the positive marker of option (iii) may be a second positive marker. This means that the positive marker of the device or positive marker conjugate of option (ii) will be different to the positive marker of the device or positive marker conjugate of option (iii) when both are present in an assay device of the invention.

Where an assay device of the invention includes immobilised capture species for reducing the quantity of labelled conjugate that reaches the detection zone in the absence of a first positive marker, the assay device may also include any suitable reagents and immobilised capture species disclosed herein for reducing the quantity of labelled conjugate that reaches the detection zone in the absence of a second positive marker. This concept can be extended to reduce the quantity of labelled conjugate that reaches the detection zone in the absence of further positive markers.

In an embodiment, the device does not comprise any means for reducing the quantity of labelled conjugate that reaches the detection zone in the absence of a positive marker. In an embodiment, the device does not comprise any means for reducing the quantity of labelled conjugate that reaches the detection zone in the presence of a negative marker.

The invention also provides a method of conducting an assay using the assay device of the invention, the method comprising:
(i) applying a sample to the assay device,
(ii) determining the result of the assay at the detection zone, without reference to any capture zone present in the device.

DETAILED DESCRIPTION

The present invention is based in part on the realization that there is a need to improve specificity of tests for an analyte. In traditional assay devices, a positive assay result indicative of the presence of a first condition in a subject may be based on identifying the presence of an analyte in a sample from the subject (for example by observing the accumulation of detectable label associated with the analyte at a detection zone of an assay device). However, if the analyte is associated with more than one condition, there is a risk that the presence of the analyte does not necessarily mean that the first condition is present in the subject. The present invention addresses this problem by utilizing the presence or absence of additional markers in the sample from the subject to modulate the ability of the assay device to produce a detectable signal at a detection zone in response to the presence of analyte in the sample. The present invention contemplates the use of the presence of one or more negative markers in the sample to reduce the quantity of a labelled conjugate associated with the analyte that reaches the detection zone and generates a signal. The present invention also contemplates the use of the absence of one or more positive markers in the sample to reduce the quantity of a labelled conjugate associated with the analyte that reaches the detection zone and generates a signal. Both strategies alone or in combination reduce the risk that a signal is generated at the detection zone (i.e. a positive assay result is observed) when the first condition is not present in the subject.

One non-limiting example of this principle is in the context of a pregnancy test. In this example, the analyte indicative of pregnancy (but that may also be present in another condition e.g. menopause or peri-menopause) is hCG. According to the invention, a negative marker for pregnancy, such as FSH (which is elevated in peri/post menopause), can be used to reduce the quantity of labelled conjugate associated with hCG that reaches a detection zone and generates a signal. In this example, a reagent zone may include a mobilizable labelled conjugate that can become associated with both hCG and FSH (for example, it may comprise an anti-hCG antibody and an anti-FSH antibody). A capture zone for FSH (not visible to the user, or visible but not interpreted by the user, or indeed not measured by the device) can be provided downstream of the reagent zone and upstream of the detection zone. If the sample contains hCG and no FSH, the mobilizable labelled conjugate becomes associated with hCG, passes through the capture zone and binds at the detection zone, such that a signal is observed at the detection zone, indicating that the subject is pregnant. If the sample contains hCG and FSH (for example because the subject is peri-menopausal), the mobilizable labelled conjugate can become associated with hCG and FSH to form a complex. The complex is captured at the FSH capture zone such that it cannot travel to the detection zone. Therefore, even though the sample contains hCG, the quantity of labelled conjugate that reaches the detection zone and generates an observable signal is reduced relative to the quantity of labelled conjugate that would reach the detection zone in the presence of hCG and the absence of FSH.

According to the invention, a positive marker for pregnancy, such as P3G, can be used to modulate the quantity of labelled conjugate associated with the analyte that reaches a detection zone and generates a signal. For example, a reagent zone may include a mobilizable labelled conjugate that can become associated with both hCG and P3G (for example, it may comprise an anti-hCG antibody and an anti-P3G antibody). A capture zone (not visible to the user, or visible but not interpreted by the user, or indeed not measured by the device) may be provided downstream of the reagent zone and upstream of the detection zone and may include a P3G conjugate. A detection zone may comprise, for example, an anti-hCG antibody. If the sample contains hCG and P3G, the mobilizable labelled conjugate can become associated with the hCG and the P3G to form a complex, preventing the P3G conjugate at the capture zone from capturing the complex. The complex passes through the capture zone and binds at the detection zone, via the hCG in the sample, such that a signal is observed at the detection zone, indicating that the subject is pregnant. If the sample contains hCG and no P3G, the mobilizable labelled conjugate can become associated with the hCG to form a complex. The labelled regent is captured by the P3G conjugate at the capture zone, preventing it from travelling to the detection zone. Therefore, even though the sample contains hCG, the quantity of labelled conjugate that reaches the detection zone and generates an observable signal is reduced. In an alternative arrangement, the P3G conjugate can instead be provided on the mobilisable conjugate and a capture zone can be provided with an immobilised capture species configured to capture P3G or the P3G conjugate (e.g. an anti-P3G antibody). In such an embodiment, if P3G is present in the sample, it is captured at the capture zone, meaning that labelled conjugate comprising P3G conjugate is not captured at the capture zone and can proceed to the detection zone where it can interact via hCG in the sample and produce a signal at the detection zone. If hCG is present in the sample but P3G is not present in the sample, the mobilisable conjugate will be captured by the immobilised capture species at the capture zone and cannot proceed to the detection zone. Therefore, even though the sample contains hCG, the quantity of labelled conjugate that reaches the detection zone and generates an observable signal is reduced relative to the quantity labelled conjugate that would reach the detection zone in the presence of hCG and the presence of P3G.

One application of the present invention is to provide an improved high-sensitivity pregnancy test having improved specificity, which allows earlier determination of pregnancy. Such an improved pregnancy test is particularly useful for individuals who are peri-menopausal or post-menopausal, because there is a reduced risk of a positive result being obtained when the individual is not pregnant as a result of small amounts of pituitary-derived hCG in the test sample. It will be appreciated that this principle can be applied to other analytes and markers, including those associated with other conditions. For example, one can envisage an assay to test for disease X based on the identification of analyte A in a sample. Analyte A is also present in condition Y. Negative marker N is present at relatively high levels in condition Y and absent or at relatively (significantly) low levels in disease X. An assay device of the invention could include a mobilisable labelled conjugate comprising binding reagent for analyte A and a binding reagent for negative marker N, a capture zone comprising an immobilised capture species comprising a binding reagent for negative marker N, and a detection zone comprising immobilised binding reagent for analyte A. If negative marker N and analyte A are present in a sample applied to the device (because condition Y rather than disease X is present in the subject from which the sample is derived), N is bound by the labelled conjugate to form a complex that is bound at the capture zone. The capture zone therefore reduces the quantity of the labelled conjugate that reaches the detection zone and forms a detectable signal in the presence of analyte A when negative marker N is present in the sample. Therefore, the risk that a positive result indicative of the presence of disease X is reduced, particularly when testing a sample containing analyte A in the existence of condition Y improving the specificity of the test.

In another example, an assay to test for disease X may be based on the identification of analyte A in a sample. Analyte A is also present in condition Y. Positive marker P is present at relatively high levels in disease X and absent or at relatively (significantly) low levels in condition Y. An assay device of the invention could include a mobilisable labelled conjugate comprising binding reagent for analyte A and a binding reagent for positive marker P, a capture zone comprising an immobilised positive marker or positive marker conjugate, and a detection zone comprising immobilised binding reagent for analyte A. If positive marker P and analyte A are present in the sample, binding reagent for positive marker P binds positive marker P in the sample, preventing the labelled conjugate from being captured by the immobilised positive marker or positive marker conjugate at the capture zone. The labelled conjugate can proceed to the detection zone where it is captured by the immobilised binding reagent for analyte A, hence producing a signal at the detection zone indicative of the presence of disease X. If analyte A is present in the sample and positive marker P is absent from the sample, the binding reagent for positive marker P of the labelled conjugate will bind the immobilised positive marker or positive marker conjugate at the capture zone, preventing the labelled conjugate from reaching the detection zone. The capture zone therefore reduces the quantity of the labelled conjugate that reaches the detection zone and forms a detectable signal in the presence of the analyte when positive marker P is absent from the sample.

The device of the invention can be adapted to include mobilisable reagents and immobilised capture species to reduce the quantity of labelled conjugate that reaches the detection zone in the presence of any number of additional negative markers, and/or in the absence of any number of additional positive markers.

Assay Flow Path

The assay device of the invention comprises an assay flow path In an embodiment, the flow path comprises a reagent zone, one or more capture zones and a detection zone. The or each capture zone is downstream of the reagent zone, and the detection zone is downstream of the or each capture zone.

"Upstream" and "downstream" are used to describe the position of components of the assay device with reference to the direction of flow of sample applied to the device. If component A is upstream of component B and/or component B is downstream of component A, sample applied to the device (at the intended sample application site) will reach component A before reaching component B.

Dried binding reagents may be provided in the flow path of a microfluidics device or on a porous carrier material provided upstream from a porous carrier material comprising a detection zone in a lateral flow type device. The upstream porous carrier material may be macroporous. The macroporous carrier material should be low or non-protein-binding, or should be easily blockable by means of reagents such as BSA or PVA, to minimise non-specific binding and to facilitate free movement of the labelled reagent after the macroporous carrier has become moistened with the liquid sample. The macroporous carrier material can be pre-treated with a surface active agent or solvent, if necessary, to render it more hydrophilic and to promote rapid uptake of the liquid sample. Further, one or more sugars (e.g. sucrose, trehalose) may be used to stabilize and help mobilise the labelled reagent. These may be applied to the flow path and/or to the porous carrier material conveniently as part of a solution in which the labelled reagent is applied to the porous carrier. Suitable materials for a macroporous carrier include plastics materials such as polyethylene and polypropylene, or other materials such as paper or glass-fibre. In the case that the labelled binding reagent is labelled with a detectable particle, the macroporous carrier may have a pore size at least ten times greater than the maximum particle size of the particle label. Larger pore sizes give better release of the labelled reagent.

The assay flow path may comprise a lateral flow porous carrier. The porous carrier material is typically one that has a high protein binding capacity which, after application of reagents to form the immobilised capture and detection zones, is blocked by means of reagents such as BSA or PVA, to minimise non-specific binding and to facilitate free movement of the labelled conjugate after the macroporous carrier has become moistened with the liquid sample. Suitable materials that may be employed as a porous carrier include nitrocellulose, acetate fibre, cellulose or cellulose derivatives, polyester, polyamide, polyolefin or glass fibre. The porous carrier may comprise nitrocellulose. This has the advantage that a binding reagent can be immobilised firmly without prior chemical treatment. If the porous solid phase material comprises paper, for example, immobilisation of an antibody may be performed by chemical coupling using, for example, CNBr, carbonyldimidazole, or tresyl chloride. The test device may comprise a sample application zone. This is a zone of porous (typically bibulous) material to which an aqueous sample, such as urine, may be applied.

An alternative to a lateral flow type assay flow path is a "flow through" assay device. In such a device, sample flows substantially vertically rather than laterally. Preferably the device comprises a sample application zone, one or more membranes comprising one or more capture zones as described herein disposed vertically or substantially vertically below the application zone, and a membrane comprising a detection zone as described herein disposed vertically or substantially vertically below the one or more capture zone membranes. Sample is applied to the sample application zone and flows downwards through the or each capture zone membrane to the detection zone membrane. An assay result may be determined by viewing or reading the detection zone, for example from the underside of the flow through device. A flow through assay device may or may not include a reagent zone as described herein. If a reagent zone is provided, this may be present in a further membrane provided upstream (in a generally vertical direction) from the capture zone membrane(s). Such a reagent zone may include any reagents described herein (e.g. labelled conjugate) in a dried state. Alternatively, or additionally, reagents such as the labelled conjugate as described herein may be provided in the vicinity of the capture zone membrane(s) in a dried state. Alternatively, labelled conjugate may be provided separately and applied to the device before or after the sample is applied, or together with the sample. For example, such reagents could be mixed with the sample before application to the device. The invention includes a kit comprising a flow through assay device as described herein, labelled reagent as described herein and optionally any other reagent (e.g. reagents provided in the reagent zone) described herein.

Typically, sample is applied to the sample application zone by the user urinating directly onto the sample application zone. Alternatively, the sample application zone may be dipped into a container of sample. In the case where the sample is blood, serum or plasma the sample may be applied to the device using a pipette or other instrument and may be followed by addition of an elution buffer to mobilise the sample components along the assay flow path.

The sample application zone is preferably upstream of the reagent zone.

An absorbent "sink" can be provided at a distal, downstream end of the assay flow path. The absorbent sink may preferably comprise a highly absorbent material such as, for example, CF7 Whatman paper, and should provide sufficient absorptive capacity to remove any unbound label from the vicinity of the detection zone. As an alternative to such a sink it can be sufficient to have a length of porous solid phase material which extends beyond the detection zone. An advantage of providing a highly absorbent sink is that it removes or substantially removes excess labelled binding reagent from the assay flow path. This has the effect of minimising the extent of unbound labelled binding reagent in the vicinity of respective zones. Removing or reducing unbound labelled reagent from the vicinity of the detection zone (as well as from a control zone, where present) helps provide the correct determination of the test result.

Reagent Zone

The reagent zone of assay devices of the invention comprises a mobilisable labelled conjugate comprising a detectable label.

A "mobilisable" entity is one that is associated with a substrate, such as a component of an assay flow path, in the dry state, and is mobilised when contacted with fluid and able to flow along the substrate.

"Label" when used in the context of a labelled conjugate refers to any substance which is capable of producing a signal that is detectable by visual or instrumental means. Various labels suitable for use in the present invention include labels which produce signals through either chemical or physical means, such as being optically detectable. Such labels include enzymes and substrates, chromogens, catalysts, fluorescent compounds, chemiluminescent compounds, electroactive species, dye molecules, radioactive labels and particle labels. Particle labels may include magnetic or electronically charged labels, which can be detected by magnetic or electrochemical means. The label may be covalently attached to a binding reagent. The label may be optically detectable. Preferred optically detectable labels include colloidal metallic particle labels and dye-laden particles, as below.

The label may comprise a colloidal metallic particle such as gold, silver, platinum, silver enhanced gold sol, carbon sol, or carbon nanoparticles; colloidal metalloid or non-metallic particles such as tellurium or selenium; or dyed or coloured particles such as a polymer particle incorporating a dye, or a dye sol. The dye may be of any suitable colour, for example blue. The dye may be fluorescent, or comprise a quantum dot. Suitable fluorescent materials are well-known to those skilled in the art. Dye sols may be prepared from commercially-available hydrophobic dyestuffs such as Foron Blue SRP (Sandoz) and Resolin Blue BBLS (Bayer). Suitable polymer labels may be chosen from a range of synthetic polymers, such as polystyrene, polyvinyltoluene, polystyrene-acrylic acid and polyacrolein. The monomers used are normally water-insoluble, and are emulsified in aqueous surfactant so that monomer micelles are formed, which are then induced to polymerise by the addition of initiator to the emulsion. Substantially spherical polymer particles are produced. An ideal size range for such polymer particles is from about 0.05 µm to about 0.5 µm. Larger polymer particles can also be used once coupled to an appropriately sized porous membrane. According to an exemplary embodiment the label is a gold colloid with a preferred particle mean diameter in the range 0.02 µm to 0.25 µm. In an embodiment, the label is blue latex. In an embodiment, the label is gold sol. In an embodiment, the label is 40 nm gold sol.

For present purposes, the term "binding reagent" refers to a member of a binding pair, i.e., two different molecules wherein one of the molecules binds the second molecule through chemical and/or physical means. The two molecules are related in the sense that their binding with each other is such that they are capable of distinguishing their binding partner from other assay constituents having similar characteristics. The members of the binding pair may be referred to as ligand and receptor (antiligand), a binding pair member and binding pair partner, and the like. A molecule may also be a binding pair member for an aggregation of molecules; for example an antibody raised against an immune complex of a second antibody and its corresponding antigen may be considered to be an binding pair member for the immune complex. A binding reagent is typically a specific binding reagent. For example, a binding reagent may specifically bind to the alpha subunit of hCG and to the alpha subunit present on FSH, Luteinizing Hormone (LH) or Thyroid Stimulating Hormone (TSH). A specific binding reagent could be a binding reagent that binds the beta subunit of hCG.

A binding reagent may consist of or comprise antibody. The term "antibody" as used herein encompasses both whole antibodies and antigen-binding fragments thereof. Antigen-binding fragments can be produced by conventional techniques. Examples of such fragments include, but are not limited to, Fab, F(ab')$_2$, and Fv fragments. A binding reagent may consist of or comprise an aptamer. A binding reagent may consist of or comprise an affimer. Binding reagents such as antibodies for use in the invention are commercially available from various supplies, such as, for example, Medix Biochemica Espoo, Finland.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding reagent.

In some embodiments, the mobilisable labelled conjugate comprises means for associating the labelled conjugate with the analyte and means for associating the labelled conjugate with a first negative marker which may be present in the sample.

The means for associating the labelled conjugate with the analyte may comprise or consist a binding reagent. The binding reagent may bind the analyte directly or indirectly. If the binding reagent binds the analyte indirectly, a mobilisable analyte binding reagent, linked to a first binding partner can be provided separately from the labelled conjugate, for example, in the reagent zone. In such embodiments, the labelled conjugate may be provided with a second binding partner for the first binding partner. In this way, the binding reagent for the analyte can be located at the labelled conjugate without being directly linked to the labelled conjugate. The first and second binding partners can be any suitable binding partners that are specific for one another (e.g. antibody-antigen). Examples include binding reagent pairs such as biotin and streptavidin, biotin and anti-biotin antibody, fluorescein and anti-fluorescein antibody.

Either member of the binding pair could be linked to the labelled conjugate, with the other partner being provided, for example in the reagent zone or elsewhere along the flow path but upstream of the capture zone(s). This concept could be adapted to include further intermediate binding partners. This concept could be adapted to locate other binding members disclosed herein at a desired position on the assay flow path.

The means for associating the labelled conjugate with the analyte may comprise or consist of an antibody, for example an antibody that binds an epitope of the analyte.

The means for associating the labelled conjugate with a first negative marker may comprise or consist of a binding reagent. The binding reagent may bind the first negative marker directly or indirectly. If the binding reagent binds the first negative marker indirectly, a mobilisable first negative marker binding reagent, linked to a first binding partner can be provided separately from the labelled conjugate, for example, in the reagent zone. In such embodiments, the labelled conjugate may be provided with a second binding partner for the first binding partner. In this way, the binding reagent for the first negative marker can be located at the labelled conjugate without being directly linked to the labelled conjugate. The first and second binding partners can be any suitable binding partners that are specific for one another (e.g. antibody-antigen). Examples include binding reagent pairs such as biotin and streptavidin, biotin and anti-biotin antibody, fluorescein and anti-fluorescein antibody.

Either member of the binding pair could be linked to the labelled conjugate, with the other partner being provided, for example in the reagent zone or elsewhere along the flow path but upstream of the capture zone(s). This concept could be adapted to include further intermediate binding partners. This concept could be adapted to locate other binding members disclosed herein at a desired position on the assay flow path.

The means for associating the labelled conjugate with a first negative marker may comprise or consist of an antibody, for example an antibody that binds an epitope of the first negative marker.

The means for associating the labelled conjugate with the analyte and means for associating the labelled conjugate with a first negative marker may be identical. For example, the labelled conjugate may be directly or indirectly linked to an antibody that can bind either the analyte or the first negative marker. The antibody may bind an epitope that is shared by the analyte and the first negative marker. The antibody may bind a structural domain that is shared by the analyte and the first negative marker. Where the analyte is hCG and the first negative marker is FSH, the mobilizable labelled conjugate may comprise an antibody that binds the alpha subunit of hCG. FSH and hCG are both hetero-dimeric molecules, comprising $\alpha$ and $\beta$ subunits. The $\alpha$-subunit of FSH and hCG is essentially identical, such that antibodies directed to the a subunit may bind to both FSH and hCG. In some embodiments, the means for associating the labelled conjugate with the analyte and means for associating the labelled conjugate with a first negative marker are different. For example, the labelled conjugate may be linked directly or indirectly linked to an antibody that binds the analyte but not the first negative marker and also linked directly or indirectly linked to an antibody that binds the first negative marker but not the analyte.

In some embodiments, the mobilisable labelled conjugate comprises a positive marker or positive marker conjugate the positive marker portion of which is accessible for binding. The positive marker or positive marker conjugate may be linked to or otherwise associated with means for associating the labelled conjugate with the analyte. Where the positive marker is a hapten, preferably it is conjugated with another moiety, such as a carrier, to form a positive marker conjugate. Larger positive markers may or may not be conjugated to another moiety. Larger (non-hapten) positive markers may be immobilised directly on the mobilizable labelled conjugate e.g. by physical absorption or chemical coupling. However, it may be preferable to link non-hapten positive markers to another moiety, for example, if direct immobilisation has a detrimental impact on the structure of the positive marker or its ability to participate in binding reactions. The positive marker may be a progesterone metabolite, such as P3G. The means for associating the labelled conjugate with the analyte may be any means for associating a labelled conjugate with the analyte disclosed herein. A positive marker/positive marker conjugate may be conjugated to a binding reagent for the analyte, which is linked to the labelled conjugate directly or indirectly in the manner discussed herein. For example, where the analyte is hCG and the positive marker is a progesterone metabolite, such as P3G, a progesterone metabolite, such as P3G may be conjugated to an anti-hCG antibody, such as an anti-alpha hCG antibody. Alternatively or additionally, a mobilisable positive marker or positive marker conjugate may be provided separately in the reagent zone. In this case, the mobilizable positive marker or positive marker conjugate is capable of associating with the labelled conjugate following mobilisation such that, when the labelled conjugate is associated with the positive marker or positive marker conjugate, the positive marker or positive marker portion of the conjugate is accessible for binding. To facilitate this association, the labelled conjugate and positive marker/positive marker conjugate may each comprise a member of a binding pair, such that when the members of the binding pair contact each other, the labelled conjugate becomes associated with the positive marker/positive marker conjugate. The first and second binding partners can be any suitable binding partners that are specific for one another (e.g. antibody-antigen). When fluid contacts the positive marker or positive marker conjugate, the positive marker or positive marker conjugate is mobilised and can associate with the labelled conjugate. Examples of binding pairs include biotin and streptavidin, biotin and anti-biotin antibody, fluorescein and anti-fluorescein antibody. Either one of the partners could be linked to the labelled conjugate, with the other partner (linked to the positive marker or positive marker conjugate) being provided, for example in the reagent zone or elsewhere along the flow path but upstream of the capture zone(s). This concept could be adapted to include further intermediate binding partners.

The positive marker conjugate comprises a positive marker portion. The positive marker portion is accessible for binding by a binding agent, such as an antibody. The positive marker conjugate may comprise a progesterone metabolite, such as P3G, or portion thereof. The positive marker conjugate may comprise a protein carrier, such as BSA, ovalbumin or a mouse antibody.

In some embodiments, the mobilisable labelled conjugate comprises means for associating the labelled conjugate with a positive marker, or a positive marker conjugate. The means for associating the labelled conjugate with a positive marker/positive marker conjugate may comprise or consist of a binding reagent. The binding reagent may bind the positive marker or positive marker conjugate directly or indirectly. If the binding reagent binds the positive marker or positive marker conjugate indirectly, a mobilisable binding reagent for the positive marker/positive marker conjugate, linked to a first binding partner, can be provided separately from the labelled conjugate, for example, in the reagent zone, or elsewhere along the flow path but upstream of the capture zone(s). In such embodiments, the labelled conjugate may be provided with a second binding partner for the first binding partner. In this way, the binding reagent for the positive marker/positive marker conjugate can be located at the labelled conjugate without being directly linked to the labelled conjugate. The first and second binding partners can be any suitable binding partners that are specific for one another (e.g. antibody-antigen). Examples include biotin and streptavidin, biotin and anti-biotin antibody, fluorescein and anti-fluorescein antibody. Either one of the partners could be linked to the labelled conjugate, with the other partner (linked to the binding reagent for the positive marker/positive marker conjugate) being provided, for example in the reagent zone or elsewhere along the flow path but upstream of the capture zone(s). This concept could be adapted to include further intermediate binding partners.

The means for associating the labelled conjugate with a positive marker, or a positive marker conjugate, may comprise or consist of an antibody, for example an antibody that binds an epitope of the positive marker. For example, where the positive marker is P3G, the means for associating the labelled conjugate with a positive marker, or a positive marker conjugate, may comprise or consist of an anti-P3G antibody.

In some embodiments, the reagent zone further comprises a mobilisable positive marker or positive marker conjugate for immobilisation for example at the capture zone(s) downstream of the reagent zone. This mobilisable positive marker/positive marker conjugate may comprise or be linked to one member of a binding pair. The other member of the binding pair is provided downstream of the reagent zone, for example in a capture zone. The mobilisable positive marker/positive marker conjugate can therefore be immobilised at the capture zone such that it is available for association with means for associating the labelled conjugate with the positive marker/positive marker conjugate. Examples of binding pairs include biotin and streptavidin, biotin and anti-biotin antibody, fluorescein and anti-fluorescein antibody. Either one of the partners could be linked to the mobilizable positive marker/positive marker conjugate, with the other partner being provided, for example in a capture zone. This concept could be adapted to include further intermediate binding partners.

Capture Zone(s)

The device of the invention comprises one or more capture zones, positioned downstream of the reagent zone and upstream of the detection zone. The function of the one or more capture zones is to ensure that the detection of the labelled conjugate at the detection zone reliably indicates the presence of the first condition in a subject from which the sample is derived. This is achieved by (i) capturing labelled conjugate at the capture zone(s) when the sample contains one or more negative markers, which are preferably markers indicative of the absence of the first condition, such that the amount of the labelled conjugate reaching the detection zone is reduced, and/or (ii) capturing labelled conjugate at the capture zone(s) unless the sample contains one or more positive markers, which are preferably markers indicative of the presence of the first condition, such that the amount of labelled reagent reaching the detection zone is reduced. Hence in the presence of a negative marker and/or in the absence of a positive marker, the capture zone(s) reduce the amount of labelled conjugate: reaching the detection zone thereby reducing the likelihood that the detection zone will produce a detectable signal even in the presence of a small amount of analyte. This means that the likelihood of a false positive i.e. an indication that the first condition is present when it is not, is reduced, improving the specificity of the test. Advantageously, not only can the capture zone(s) reduce the amount of labelled conjugate reaching the detection zone but the capture zone(s) can also reduce the amount of analyte reaching the detection zone, since complexes captured at the capture zone(s) may also comprise analyte. This dual effect significantly reduces the risk that signal is detected at the detection zone when the test sample is derived from a subject who does not have the first condition.

Preferably, the device does not comprise a capture zone that includes an immobilised capture species capable of binding the analyte.

A capture zone may be designed to utilise the presence of one or more negative markers in the sample to reduce the quantity of a labelled conjugate (which may be associated with the analyte) that reaches the detection zone.

A capture zone may be designed such that one or more negative markers present in the sample reduce the quantity of labelled conjugate (which may be associated with the analyte) that reaches the detection zone. A capture zone may comprise immobilised capture species configured to capture a complex comprising the labelled conjugate and first negative marker. Capture of the complex is preferably achieved by a specific binding reaction with first negative marker. Preferably, the binding reaction occurs with an epitope of the first negative marker that is different to an epitope bound by means for associating the labelled conjugate with a first negative marker of the mobilizable labelled conjugate, such that a "sandwich" can form. The captured complex may further comprise the analyte, when analyte is present in the sample. Preferably, the immobilised capture species for the negative marker is configured not to capture complexes that do not comprise the first negative marker.

One or more capture zones may comprise an immobilised capture species that is specific for the first negative marker. In some embodiments, when a sample containing first negative marker is applied to the assay device, the first negative marker associates with the labelled conjugate via the means for associating the labelled conjugate with a first negative marker, forming a first negative marker-labelled conjugate complex. If the analyte is also present in the sample, the complex may further comprise the analyte since the labelled conjugate is able to bind both the analyte and the negative marker. When the complex reaches a capture zone comprising an immobilised capture species configured to capture a complex comprising the labelled conjugate and the first negative marker, the complex is captured and cannot flow to the detection zone. Thus, the presence of the first negative marker in the sample can prevent or reduce the total amount of the labelled conjugate reaching the detection zone and producing a detectable signal, even if the analyte is also present in the sample. This also effectively reduces the amount of analyte reaching the detection zone further reducing the signal at the detection zone in a sample comprising the analyte and the negative marker.

Immobilised capture species may bind the first negative marker directly. Immobilised capture species may bind an epitope of the first negative marker that is not present in the analyte. Immobilised capture species may comprise or consist of an antibody. The antibody may bind an epitope of the first negative marker that is not present on the analyte. Where the first negative marker is FSH, a capture zone may comprise immobilised anti-FSH specific antibody, for example an anti-beta FSH antibody.

A capture zone may comprise immobilised capture species that binds the first negative marker indirectly. For example, in some embodiments, a mobilisable first negative marker binding reagent that is specific for the first negative marker, linked to a first binding partner can be provided, for example in the reagent zone or elsewhere along the flow path but upstream of the capture zone(s). Mobilisable first negative marker binding reagent may bind an epitope of the first negative marker that is not present in the analyte. The or each capture zone may be provided with an immobilised second binding partner for the first binding partner. In this way, the mobilisable first negative marker binding reagent can be located at the capture zone without being directly immobilised to the flow path. The first and second binding partners can be any suitable binding partners that are specific for one another (e.g. antibody-antigen). Examples include binding reagent pairs such as biotin and streptavidin, biotin and anti-biotin antibody, fluorescein and anti-fluorescein antibody. Either member of the binding reagent pair could be immobilised at the capture zone, with the other member (linked to the binding reagent for the negative marker) being provided, for example, in the reagent zone or elsewhere along the flow path but upstream of the capture zone(s). This concept could be adapted to include further intermediate binding partners. This concept could be adapted to locate other binding members disclosed herein at a desired position on the assay flow path. In an embodiment, the reagent zone includes a mobilizable anti-beta FSH antibody labelled with a first member of a binding pair (e.g. biotin), and a capture zone comprises an immobilised second member of the binding pair e.g. anti-biotin antibody or streptavidin. In this way, the anti-beta FSH antibody can be located at a capture zone without being directly immobilised at the capture zone. This concept can be applied to capture zones for other negative markers.

Alternatively, or additionally a capture zone may be designed to utilise the absence of one or more positive markers in the sample to reduce the quantity of a labelled conjugate (which may be associated with the analyte) that reaches the detection zone.

The presence of a positive marker in the sample reduces the likelihood of labelled conjugate being captured in the capture zone, for example by occupying positive marker binding sites at the capture zone or at the labelled conjugate.

In some embodiments, at least one capture zone comprises an immobilised capture species configured to capture a positive marker or labelled conjugate comprising or associated with a positive marker/positive marker conjugate. Capture of the labelled conjugate is preferably achieved by a specific binding reaction with positive marker/positive marker conjugate. Positive marker present in the sample is bound by (and hence may occupy) a binding site of the immobilised capture species such that the binding site is not available to capture labelled conjugate comprising or associated with positive marker/positive marker conjugate. Labelled conjugate comprising or associated with positive marker/positive marker conjugate can therefore proceed to the detection zone (unless prevented from doing so by other capture means disclosed herein).

Positive marker in the sample may compete with the positive marker/positive marker conjugate of the device for binding at a capture zone. When positive marker is not present in the sample, the immobilised capture species captures labelled conjugate comprising or associated with positive marker/positive marker conjugate of the device, thereby preventing the labelled conjugate proceeding to the detection zone. The immobilised capture species may bind the positive marker or positive marker conjugate directly. The immobilised capture species may comprise or consist of an antibody. Where a positive marker is P3G, the capture zone may comprise an immobilised anti-P3G antibody.

A capture zone may comprise immobilised capture species that captures positive marker or positive marker conjugate indirectly. For example, in some embodiments, a mobilisable binding reagent for positive marker/positive marker conjugate, linked to a first binding partner, can be provided, for example in the reagent zone or elsewhere along the flow path but upstream of the capture zone(s). In such embodiments, the or each capture zone may be provided with an immobilised second binding partner for the first binding partner. In this way, the mobilisable binding reagent for the positive marker/positive marker conjugate can be located at the capture zone without being directly immobilised to the flow path. The first and second binding partners can be any suitable binding partners that are specific for one another. Examples include binding reagent pairs such as biotin and streptavidin, biotin and anti-biotin antibody, fluorescein and anti-fluorescein antibody. Either member of the binding reagent pair could be immobilised at the capture zone, with the other member being provided, for example, in the reagent zone. This concept could be adapted to include further intermediate binding partners.

In an embodiment, the reagent zone includes a mobilizable anti-P3G antibody labelled with a first member of a binding pair (e.g. biotin), and a capture zone comprises an immobilised second member of the binding pair e.g. anti-biotin antibody or streptavidin. In this way, the anti-P3G antibody can be located at a capture zone without being directly immobilised at the capture zone. This concept can be applied to capture zones for other positive markers.

In some embodiments, at least one capture zone comprises an immobilised capture species configured to capture labelled conjugate comprising means for associating the labelled conjugate with a positive marker or positive marker conjugate. Capture of the labelled conjugate is preferably achieved by a specific binding reaction with the means for associating the labelled conjugate with a positive marker or positive marker conjugate. The immobilised capture species may comprise or consist of an immobilised positive marker or positive marker conjugate. Where the positive marker is a hapten, preferably it is conjugated with another moiety, such as a carrier, to form a positive marker conjugate. Larger positive markers may or may not be conjugated to another moiety. Larger (non-hapten) positive markers may be immobilised directly to the flow path. However, it may be preferable to link non-hapten positive markers to another moiety, for example, if direct immobilisation has a detrimental impact on the structure of the positive marker or its ability to participate in binding reactions. Alternatively or additionally, the reagent zone may comprise a mobilisable positive marker or positive marker conjugate. In this case, at least one capture zone comprises an immobilised capture species for locating the mobilisable positive marker or positive marker conjugate at the capture zone such that the positive marker or positive marker portion of the conjugate is accessible for binding. In this way, the positive marker conjugate can be located at a capture zone without it being directly immobilised to the flow path. Locating the positive marker or positive marker conjugate at a capture zone can be achieved using any of the binding reagent pairs disclosed herein. Where a positive marker or positive marker conjugate is (directly or indirectly) immobilised at the capture zone, the mobilisable labelled conjugate comprises means for associating the labelled conjugate with a positive marker. When the positive marker is not present in the sample, labelled conjugate is captured by positive marker or positive marker conjugate immobilised or located in the capture zone. Captured labelled conjugate is prevented from proceeding to the detection zone. When the positive marker is present in the sample, it becomes associated with the labelled conjugate, such that the labelled conjugate is not captured by the positive marker/positive marker conjugate immobilised or located in the capture zone, and can proceed to the detection zone. Where the positive marker is P3G, preferably the device comprises a P3G conjugate. In an embodiment, the reagent zone includes a mobilizable P3G conjugate labelled with a first member of a binding pair (e.g. biotin), and a capture zone comprises an immobilised second member of the binding pair e.g. anti-biotin antibody or streptavidin. In this way, the P3G/P3G conjugate can be located at a capture zone without being directly immobilised at the capture zone. This concept can be applied to capture zones for other positive markers.

In an embodiment, the device is arranged such that, in use, the or each capture zone is not visible to a user. In an embodiment, the or each capture zone is not readable by assay reading means. In an embodiment, no capture zones included in the device are visible to a user when the device is in use. In an embodiment, where the capture zone(s) may be totally or partially visible to the user the device is provided as part of a kit which further includes instructions to a user to disregard any signal that develops at a capture zone and/or to determine the result of the assay based on the presence or absence of signal at the detection zone without reference to any capture zone. In an embodiment, the device is provided as part of a kit which comprises an accessory for obscuring one or more capture zones or all capture zones present in the device.

In an embodiment the capture zone(s) may be visible to the user who may be instructed to capture an image or video of the device on a mobile device such as a mobile phone which in turn interprets the result of the test either itself or by some other device directly or indirectly connected to the mobile device. In this instance the processing/analysis to derive the test result does not encompass any reference to or indeed measurement of the capture zone(s).

Preferably no capture zones are readable by assay reading means. In an embodiment, the assay device does not comprise assay reading means. In an embodiment, the assay device is not compatible with external reading means. In an embodiment, the device does not comprise means for reading or analysing the or each capture zone. The one or more capture zones may be obscured by any suitable means. For example, the assay device may comprise a housing that obscures the, or each capture zone. If the detection zone of the assay device is designed to be read by an assay reader and/or the assay device includes an assay reader for reading the detection zone, such a reader will be configured to read the detection zone and will preferably not be configured to read or analyse any capture zone. For example, only reading means for reading the detection zone may be provided. It may not be necessary to obscure a capture zone in this case, since reading means of the reader are typically aligned with the detection zone and so cannot also read a capture zone upstream of the detection zone. Preferably an assay reader for use with the assay device comprises a single reading means for reading the detection zone. In an embodiment, the assay device does not include an assay for measuring the amount of a negative marker or positive marker.

In an embodiment, the assay device is configured to allow detection, measurement or observation of a signal only at the detection zone. In an embodiment, the assay device is configured to prevent the detection, observation and/or measurement of a signal at the or each capture zone. In an embodiment, the or each capture zone is not suitable for detecting the presence or measuring the amount of labelled conjugate captured at a capture zone. In an embodiment, the device does not include means to enable a user to obtain an assay result from a capture zone. In an embodiment, the device does not include means to enable a user to detect or analyse a signal at a capture zone. Preferably, the assay device is configured such that an assay result can be obtained solely by detecting or observing signal at the detection zone (i.e. the zone at which the analyte is detected). It is not necessary for any capture zone to be visible to a user or readable by assay means when in use because the result of the assay is determined solely by viewing or analyzing the detection zone. Any signal generated at a capture zone does not need to be measured, viewed or interpreted in order to obtain an assay result. Furthermore, it is advantageous to obscure the, or each capture zone so that a user is not confused or distracted by any signal generated at a capture zone.

Immobilised capture species may be arranged on the flow path in a variety of ways. For example, the flow path may comprise one or more zones comprising immobilised capture species. A capture zone may comprise any immobilised capture species or combination of immobilised capture species disclosed herein within a capture zone. For example, immobilised capture species for capturing a complex comprising a first negative marker may be provided in the same capture zone as immobilised capture species for capturing a complex comprising a second negative marker. For example, binding reagents specific for a first negative marker and a second negative could be immobilised in the same capture zone (although they can be provided in separate capture zones). Immobilised capture species configured to capture positive marker or labelled conjugate comprising or associated with positive marker/positive marker conjugate could be provided in a capture zone comprising immobilised capture species for capturing a complex comprising a first negative marker and/or other negative marker. Immobilised capture species comprising or consisting of a positive marker/positive marker conjugate or for locating a positive marker/positive marker conjugate at a capture zone may be provided in the same capture zone as immobilised capture species for capturing a complex comprising a first negative marker and/or other negative marker. An immobilised capture species designed to capture labelled conjugate in the absence of a first positive marker may be included in the same capture zone as immobilised capture species designed to capture labelled conjugate in the absence of a second positive marker (or such capture species may be provided in separate capture zones). This concept applies to immobilised capture species for use with further negative and positive markers.

Immobilised capture species may be arranged in one or more capture lines on the assay flow path. A capture zone may comprise, 1, 2, 3, 4 or 5 or more distinct capture lines. Capture lines may be arranged in parallel. The amount of labelled conjugate captured by a capture zone can be controlled by adjusting the amount, location, arrangement and position of the immobilised capture species. For example, higher capture efficiency can be achieved by positioning immobilised capture species further downstream, by increasing the number of capture lines, and/or by using wider capture lines. The pore size of a porous carrier of the flow path in addition to variation in the size of the labelled reagent can also be used to modulate capture efficiency and hence vary the sensitivity of the test for the analyte of interest. Typically, reducing the pore size of the porous carrier improves capture efficiency.

The sensitivity of the assay to analyte and negative and positive markers can be manipulated by means known to the person skilled in the art, including varying the quantity of binding reagent and/or positive marker/positive marker conjugate associated with the mobilisable labelled conjugate, and/or varying the quantity of the reagents at the one or more capture zones or indeed the number of capture zones as well as the quantity of the labelled reagent used. Further modification can be made by changing the affinity of the binding reagents used in the device. In embodiments involving positive marker conjugate, modifications can be made to the amount of positive marker relative to carrier protein, for example that is used at the capture zone. The sensitivity of the test to any of the analytes and markers participating in the assay can hence be modified.

Detection Zone

The assay device includes a detection zone comprising immobilised binding reagent for capturing a complex comprising the labelled conjugate and the analyte. Capture of the complex at the detection zone is preferably achieved by a specific binding reaction with the analyte. Preferably, the binding reaction occurs with an epitope of the analyte that is different to an epitope bound by means for associating the labelled conjugate with the analyte such that a "sandwich" can form. Preferably, the detection zone is configured to capture the labelled conjugate only if it is part of a complex that also comprises the analyte.

The detection zone may comprise immobilised binding reagent that binds the analyte directly. The detection zone immobilised binding reagent may consist of or comprise an antibody that is specific for the analyte. In an embodiment, immobilised binding reagent in the detection zone comprises or consists of an antibody that binds an epitope of the analyte that is not present in the first negative marker.

A detection zone may comprise immobilised binding reagent that binds the analyte indirectly. For example, in some embodiments, a mobilisable binding reagent for the analyte, linked to a first binding partner can be provided, for example in the reagent zone or elsewhere along the flow path but upstream of the detection zone. The mobilisable binding reagent may bind an epitope of the analyte that is not present in the first negative marker. The detection zone may be provided with an immobilised second binding partner for the first binding partner. In this way, mobilisable binding reagent for the analyte can be located at the detection zone without being directly immobilised to the flow path. The first and second binding partners can be any suitable binding partners that are specific for one another (e.g. antibody-antigen). Examples include biotin and streptavidin, biotin and anti-biotin antibody, fluorescein and anti-fluorescein antibody. Either one of the partners could be immobilised at the detection zone, with the other partner being provided, for example in the reagent zone or elsewhere along the flow path but upstream of the detection zone. This concept could be adapted to include further intermediate binding partners. In an embodiment, the reagent zone includes a mobilizable anti-beta hCG antibody labelled with a first member of a binding pair e.g. biotin, and the detection zone comprises an immobilised second member of the binding pair e.g. anti-biotin antibody or streptavidin. In this way, the anti-beta hCG antibody can be located at the detection zone without being directly immobilised at the detection zone. This concept can be applied to other analytes.

In embodiments in which the analyte is hCG, the detection zone may comprise anti-hCG antibody such as anti-beta hCG antibody.

Capture of a complex comprising the labelled conjugate and the analyte at the detection zone results in the formation of a signal at the detection zone. The signal can be detected or examined, for example visually, or using assay reading means. Detection of the signal at the detection zone is indicative of the presence of the analyte in the sample, and the presence of the first condition in a subject from which the sample is derived. Failure to detect a signal at the detection zone, or detection of a level of signal below a certain level when measured by a reading means may be indicative of the absence of the first condition in a subject from which the sample is derived.

When using a reading means to establish the intensity of signal at the detection zone, the use of set threshold(s) could be used as part of an algorithm to establish the outcome of the test as being either: positive or negative for the first condition or indeed to quantify the signal at the detection zone to give an indication of the amount of analyte in the sample.

For example, where the analyte is hCG, detection of signal at the detection zone is indicative that the subject from which the sample is derived is pregnant. If signal is not detected at the detection zone following application of a sample to the device, this is indicative that the subject from which the sample is derived is not pregnant.

Negative and Positive Markers

The device of the invention is useful in situations where an analyte to be detected is associated with a condition of interest in a subject (a "first condition") but detection of the analyte is not, in itself, sufficient to confirm the presence of the first condition. For example, the analyte may also be associated with a second condition. The analyte may be indicative of the presence of a second condition.

In some embodiments, the analytes, negative markers and positive markers are such that one or more of the following is true:

The presence of the analyte and the positive marker in a sample is indicative of the presence of a first condition.

The presence of the negative marker and/or the absence of the analyte in a sample is indicative of the absence of a first condition.

The presence of the analyte and the negative marker in a sample is indicative of the absence of a first condition.

The presence of the analyte and the negative marker in a sample is indicative of the presence of a second condition.

The presence of the analyte and/or the absence of the positive marker in a sample is indicative of the presence of a second condition.

A negative marker may be a marker indicative that the first condition is not present. A negative marker may be a marker indicative that a second condition is present. A positive marker may be a marker indicative that the first condition is present. A positive marker may be a marker indicative that a second condition is absent.

In the context of a pregnancy test, the analyte may be hCG. A sample from a subject may contain hCG, or a metabolite of hCG derived from an embryo, and this may be indicative of pregnancy (a first condition). Examples of hCG metabolites include nicked intact hCG, free beta hCG, nicked free beta hCG, free alpha hCG, betacore fragment.

However, hCG may also be present, at low levels, in a sample due to the presence of a second condition, such as peri-menopause or menopause. In this case, hCG is produced by the pituitary gland of the subject and not an embryo. Therefore, in a conventional device using lateral flow for example, detecting low levels of hCG does not necessarily indicate that the subject is pregnant.

Negative Markers

A negative marker is preferably a marker that indicates that the first condition is not present in the subject. In the context of a pregnancy test, the first negative marker may be FSH or LH. A negative marker may be a marker indicative of folliculargenesis or other follicular growth or activity in the female e.g FSH or a metabolite of such markers. Examples of FSH and its metabolites include free beta FSH and products of proteolytic degradation.

In some embodiments, the amount of mobilisable labelled conjugate reaching the detection zone (where the analyte of interest is detected) is modulated by virtue of the level of a first negative marker in the sample. In this instance the mobilisable labelled conjugate may be coated in reagent(s) that directly or indirectly bind to both the analyte to be detected as well as the first negative marker. On running such a test with sample comprising both the analyte as well as the first negative marker, the quantity of mobilisable labelled conjugate reaching the detection zone is reduced by virtue of the presence of the negative marker. In such embodiments, the presence of the negative marker results in capture of labelled conjugate at a capture zone located upstream of the detection zone, the capture zone comprising immobilised capture species which directly or indirectly captures the labelled conjugate, preferably through an interaction with the first negative marker. The quantity of mobilisable labelled conjugate captured at the capture site may be dependent upon the level of the first negative marker in the sample. In a sample containing no or low levels of first negative marker but having a first quantity of the analyte to be detected, a relatively large quantity of the mobilisable labelled conjugate will reach the detection zone and produce a first visible signal at the detection zone. Conversely, the presence of a level of the first negative marker in the sample as well as a first quantity of analyte to be detected will result in capture of the mobilisable labelled conjugate at a capture zone and reduce the amount of mobilisable labelled conjugate reaching the detection zone, thereby reducing the signal produced at the detection zone. The sensitivity of the test to the analyte to be determined is hence modulated.

In an embodiment, the analyte to be detected is hCG indicating the first condition is present and the first negative marker is a marker that indicates the first condition is not present in the subject.

In some embodiments the first negative marker could be FSH. FSH may be present as a result of peri or post-menopause. In such embodiments, running a test with a sample from a peri or post-menopausal woman comprising FSH as the first negative marker would result in capture of mobilisable labelled conjugate at the capture zone positioned upstream of the detection zone thereby reducing the quantity of labelled reagent reaching the detection zone and hence reducing or eliminating the signal seen at the detection zone. Even if the sample from a peri or post-menopausal woman contains pituitary derived hCG (in addition to FSH), the presence of FSH causes the signal generated at the detection zone to be reduced or eliminated, indicating a negative result for the first condition.

The analyte and the first negative marker may share a common epitope. The analyte and the first negative marker may share a common structural feature, such as a subunit of the analyte. The analyte may be hCG and the first negative marker may be FSH. The first negative marker may be Lutenising Hormone (LH). In a preferred embodiment, the first negative marker is FSH.

The mobilisable labelled conjugate may comprise specific binding reagent that binds common structural feature(s) on the analyte and the first negative marker. This could for example be an antibody to the alpha subunit of the analyte hCG which will also bind to the alpha subunit of the first negative marker FSH. Running a test with a urine sample from a peri- or post-menopausal woman which comprises a level of FSH may result in some of the mobilisable labeled conjugate being captured at an anti-FSH capture zone, reducing or eliminating the signal seen at the detection zone.

In other embodiments the mobilisable labeled conjugate may comprise binding reagents that specifically bind the analyte and other binding reagents that specifically bind the first negative marker. The specific binding reagents may be permanently directly immobilised to the mobilisable labelled conjugate by passive adsorption or by covalent coupling. In other embodiments known as indirect binding means, the specific binding reagents may be indirectly associated to the mobilisable labeled conjugate prior to or on running the test. This can be achieved for example by coating the mobilisable labelled conjugate in a reagent such as avidin, streptavidin or anti-biotin and biotinylating the specific binding reagents. The specific binding reagent being associated with the mobilisable labeled conjugate either prior to running the test or upon running the test.

Positive Markers

A positive marker is preferably a marker that indicates that the first condition is present in the subject, being a marker that is present in addition to the analyte of interest. In the context of a pregnancy test, a positive marker is preferably a marker indicative of a maternal factor secreted or produced in connection with the maintenance of a pregnancy of the female e.g. progesterone or a metabolite of such a marker e.g. pregnanediol glucuronide (P3G). Other positive markers, which may, for example, be utilised in a pregnancy test in accordance with the invention, include isoforms of intact hCG, such as hyperglycosylated hCG, nicked hCG; subunits of hCG such as hCG beta core fragment, beta hCG, alpha hCG, nicked free beta hCG; Early Pregnancy Factor (EPF), Early Conception Factor (ECF), Follastatin (FST), Activin A, Inhibin A, Inhibin B, Pro-Alpha C and Pregnancy associated plasma protein A (PAPP-A).

A positive marker may be a small molecule known as a hapten, which on its own is too small to illicit an immune response when attempting to raise specific binding means or antibodies to it in an animal. On raising specific binding means to the hapten it is customary to conjugate or link the hapten to an immunogenic carrier such as a protein, for example bovine serum albumin or ovalbumin, if for use in raising antibodies in an animal. The resulting antibodies can be used in lateral flow assays to generate a competition or inhibition assay. For example, antibody raised to the hapten can be coated on a mobilisable labeled conjugate and the hapten or an analogue of the hapten can be conjugated to a carrier, typically a protein to form a hapten conjugate. The hapten conjugate can be immobilised at a zone on a porous carrier. On running a test in the absence of hapten in the sample, the mobilisable labelled conjugate binds the immobilised hapten conjugate whereas running the test in the presence of hapten reduces the binding of the mobilizable labelled conjugate at the immobilised hapten conjugate.

Conversely, the mobilisable labelled conjugate may be coated in hapten linked to a carrier and the antibody raised to the hapten may be immobilised at a zone on a porous carrier. Hapten present in a sample applied to such a device occupies sites on the antibody immobilised on the porous carrier and reduces the binding of the mobilisable labeled conjugate coated in the hapten linked to a carrier.

Such a negative correlation is typical of a competition or inhibition-type assay, which is often employed when the analyte of interest is a hapten and/or is too small to accommodate simultaneous binding of two different antibodies (e.g. as in the case of progesterone metabolites).

Binding means specific for a hapten are typically generated in mice and monoclonal antibodies selected for use in the assay. The specific binding means may be directly coated to the surface of a mobilisable labelled conjugate either by direct adsorption or by chemical coupling. The specific binding means may be coated to the surface of the mobilisable labeled conjugate by indirect means involving for example avidin-biotin or biotin and anti-biotin as described above. Such indirect binding may be pre-formed such that the specific binding means are coated on the mobilisable labelled conjugate prior to running the test or the specific binding means becomes bound to the mobilisable labelled conjugate whilst the test is being run. In the latter case, the mobilisable labelled conjugate may be coated in avidin and the biotinylated specific binding means for the hapten may be provided as a separate reagent within the test.

Protein conjugated to the hapten can be directly immobilised to a porous carrier or immobilised by virtue of chemical coupling. The protein conjugated to the hapten may be indirectly immobilised on the porous carrier, being provided as a mobile reagent in the test which, upon running the test, becomes immobilised on the porous carrier.

A positive marker conjugate preferably comprises a positive marker portion. The positive marker portion is preferably accessible for binding by a binding reagent, such as an antibody. The positive marker conjugate may comprise a progesterone metabolite, such as P3G, or portion thereof.

The mobilisable labelled conjugate may be directly bound to a positive marker or positive marker conjugate. In some embodiments, mobilisable labelled conjugate may be indirectly bound to positive marker/positive marker conjugate. Here the reagent zone may comprise means for associating the mobilisable labelled conjugate with a positive marker, or a positive marker conjugate. The means for associating the mobilisable labelled conjugate with a positive marker/positive marker conjugate may comprise a binding reagent. The binding reagent may bind the positive marker or positive marker conjugate directly or indirectly. The means for associating the mobilisable labelled conjugate with a positive marker, or a positive marker conjugate, may comprise or consist of an antibody that binds an epitope of the positive marker conjugate (this may be an epitope on a carrier protein). If the binding reagent binds positive marker or positive marker conjugate indirectly, it may bind another binding reagent provided in the reagent zone that binds the positive marker or positive marker conjugate directly or indirectly.

In some embodiments, the reagent zone further comprises a mobilisable positive marker/positive marker conjugate for immobilisation downstream of the reagent zone. This mobilisable positive marker/positive marker conjugate may comprise or be linked to one member of a binding pair. The other member of the binding pair can be provided immobilised downstream of the reagent zone, for example in a capture zone. The mobilisable positive marker/positive marker conjugate can therefore be immobilised at the capture zone such that it is available for association with means for associating the mobilisable labelled conjugate with the positive marker/positive marker conjugate.

In some embodiments, where the analyte is hCG and the positive marker is P3G, P3G may be conjugated to an anti-hCG antibody, such as an anti-alpha hCG antibody.

One or more capture zones can be positioned upstream of the detection zone. The mobilisable labelled conjugate may be coated directly or indirectly in specific binding means for the analyte of interest, for example antibodies to hCG in a test for pregnancy. In addition the mobilisable labelled conjugate may also be coated directly or indirectly in antibodies to a positive marker, for example anti-P3G antibody in the case where a positive marker is a metabolite of progesterone. In an embodiment, a porous carrier is prepared with directly or indirectly immobilised anti-hCG antibody at the detection zone to provide a signal at the detection zone in the presence of pregnancy-derived hCG by a typical sandwich assay. In such an embodiment, the porous carrier may comprise one or more capture zones positioned upstream of the detection zone, the capture zone(s) comprising immobilised hapten (P3G) conjugated to a protein carrier, for example BSA. Alternatively, specific binding means for P3G may be directly or indirectly immobilised at the capture zone(s) and the P3G conjugated to a carrier may be coated directly or indirectly onto the mobilisable labelled conjugate.

In a sample from a pregnant woman, the levels of positive marker, (P3G) are elevated alongside the levels of pregnancy derived hCG. In some embodiments, the presence of P3G reduces binding of the mobilisable labeled conjugate at the capture zone(s) allowing more of the labeled reagent to reach the detection zone where the presence of hCG results in the binding of the mobilisable labeled conjugate at the detection zone.

Conversely sample from a non-pregnant individual comprises significantly lower levels of positive marker (P3G). In some embodiments, applying such a sample to the assay device results in the mobilisable labelled conjugate being bound to the capture zone(s) reducing the amount of mobilisable labeled conjugate reaching the detection zone. A reduction in the amount of mobilisable labelled conjugate reaching the detection zone reduces the signal that develops at the detection zone resulting in a negative outcome for the pregnancy test becoming more likely.

The analysis of urine samples from pregnant women shows levels of positive marker, (for example P3G) are elevated alongside the elevated levels of pregnancy derived hCG. However, in peri or post-menopausal women, levels of positive marker are relatively lower. In accordance with certain embodiments of the invention, the lower levels of positive marker present in urine samples from peri or post-menopausal women results in more of the mobilisable labeled conjugate being bound at the capture zone(s) effectively reducing the amount of mobilisable labeled conjugate reaching the detection zone. Since the sample taken from peri or post-menopausal individuals comprises pituitary derived hCG, the signal seen at the detection zone in such embodiments is reduced as the amount of mobilisable labeled conjugate reaching the detection zone is compromised. In this instance there is more likelihood of reporting a negative result upon examination of the detection zone.

In some embodiments, where the analyte is hCG and the positive marker is a hapten, for example P3G, P3G may be conjugated to an anti-hCG antibody, such as an anti-alpha hCG antibody and the conjugate associated with the mobilisable labelled conjugate. Here the anti-alpha hCG functions as a specific binding means to both hCG (binding the mobilisable labelled conjugate at the detection zone) as well as a specific binding means to the first negative marker, for example FSH, binding the labelled conjugate at a capture zone(s) comprising immobilised capture species for FSH, in the presence of FSH. In addition the anti-alpha hCG~P3G conjugate on the mobilisable labelled conjugate serves to enable capture of the mobilizable labelled conjugate in the absence of P3G in the sample at a capture zone comprising immobilised capture species for P3G.

More than one positive marker can be used to further reduce the amount of labeled reagent reaching the detection zone, the porous carrier comprising binding means for each of the positive markers being utilized.

Where the device of the invention includes a positive marker or positive marker conjugate, the positive marker or positive marker portion of the conjugate may be an analogue or variant of the naturally occurring positive marker. Any analogue or variant can be used provided that both the analogue/variant and the naturally occurring marker can participate in the positive marker binding reactions described herein and compete for the relevant binding site.

Combination of Negative and Positive Markers and Additional Negative and/or Positive Markers Specific binding means for one or more negative markers and/or one or more positive markers may be provided within a single assay device. Such a format further improves the ability to report a negative result where the first condition is absent and a positive result where the first condition is present. In the case of a test for pregnancy, such a format further improves the ability to report a negative result in a non-pregnant sample and a positive result in the case of true pregnancy. In this instance the mobilisable labelled conjugate may be coated directly or indirectly in a specific binding means to bind both hCG and the negative marker FSH, for example an anti-alpha hCG. The mobilisable labelled conjugate may also be coated in a specific binding means which binds positive marker, for example anti-P3G. In such embodiments, the porous carrier preferably includes capture zone(s) comprising a specific binding reagent for FSH as well as one or more zones of positive marker or positive marker conjugate, for example P3G conjugated for example to BSA. The capture zone(s) may comprise individual zones for the negative and positive markers or the capture zone(s) may comprise the specific binding reagents being co-immobilised whereby the reagents are mixed together in any ratio prior to being immobilised at the capture zone(s).

In such embodiments, running a test with a sample taken from a pregnant individual having elevated levels of positive marker results in lower quantities of the mobilisable labeled conjugate being caught at the capture zone(s) and hence allows more of the mobilisable labeled conjugate to traverse to the detection zone. Since the sample also contains lower levels of the first negative marker FSH, less of the mobilisable labeled conjugate is captured at the capture zone(s) through an interaction with FSH. This results in more of the mobilisable labeled conjugate travelling to the detection zone and increases the likelihood of a signal being generated at the detection zone by virtue of the pregnancy derived hCG present in the sample. A true pregnancy sample is hence more likely to provide a positive test result following examination of the detection zone. Conversely, a true negative pregnancy sample not from a peri or post-menopausal woman comprising relatively lower levels of the positive marker P3G results in more of the mobilisable labeled conjugate being caught at the capture zone(s) reducing the amount of mobilisable labeled conjugate reaching the detection zone. Whilst the level of the negative marker can vary in such a sample, the amount of the negative marker is immaterial as the levels of pregnancy derived hCG is low resulting in a reduced/no signal being formed at the detection zone. In the case of a sample from a peri or post-menopausal woman being run on this test, the relatively higher levels of the negative marker FSH results in more of the mobilisable labeled conjugate being caught at the capture zone(s). In addition, further quantities of the mobilisable labeled conjugate are caught at the capture zone(s) due to relatively lower levels of the positive marker P3G being present in the sample. In effect, the amount of the mobilisable labeled conjugate reaching the detection zone is reduced increasing the likelihood that a negative result will be reported on examination of the detection zone. Since, in certain embodiments, the mobilisable labeled conjugate comprises an anti-alpha antibody as a specific binding means, it will also bind pituitary derived hCG in the sample from the peri or post-menopausal woman. By virtue of the mobilisable labeled conjugate being caught at the capture zone(s) through the presence of the negative marker FSH in the sample, some of the pituitary hCG will also be caught on the mobilisable labelled conjugate and not travel to the detection zone. The reduced amounts of pituitary derived hCG in the sample travelling to the detection zone further reduces the likelihood of the mobilisable labelled conjugate being bound at the detection zone, increasing the likelihood that a negative result will be reported at the detection zone on running a sample from a peri or post-menopausal individual.

The device of the invention may be adapted to include means in the reagent zone and capture zone(s) to facilitate further capture of labelled conjugate before it reaches the detection zone as a result of the presence of a second negative marker in the sample. Any of the means for capturing a complex comprising the labelled conjugate and the first negative marker described herein can be modified and included in a device of the invention to capture complexes comprising the labelled conjugate and the second negative marker. If the first negative marker is FSH, the second negative marker may be, for example, LH. If the first negative marker is LH, the second negative marker may be, for example, FSH.

Similarly, the device of the invention may be adapted to include means in the reagent zone and capture zone(s) to facilitate further capture of mobilisable labelled conjugate before it reaches the detection zone as a result of the absence of a second positive marker in the sample (e.g. when the second positive marker is a hapten). Any of the means for capturing a complex in the absence of a positive marker described herein can be modified and included in a device of the invention to capture complexes comprising the mobilisable labelled conjugate in the absence of the second positive marker in the sample. If a first positive marker is P3G, a second positive marker may be another progesterone metabolite. If a first positive marker is a progesterone metabolite other than P3G, a second positive marker may be P3G. The device of the invention could be further adapted for capture of complexes in the presence of any number of further negative markers and/or the absence of any number of further positive markers.

Relative Position of Zones

The one or more capture zones are positioned downstream of the reagent zone and upstream of the detection zone. A detection zone may be located towards the downstream end of an assay flow path, for example a porous carrier such as nitrocellulose. A capture zone can be positioned anywhere between the reagent zone and detection zone. The position can be adjusted as described herein to modulate capture efficiency. In one example, a detection zone may be located approximately 10 to 20 mm from the upstream end of a porous carrier (e.g. nitrocellulose membrane). A capture zone may be located approximately 3 to 15 mm from the upstream end of a porous carrier (e.g. nitrocellulose membrane). In an embodiment, a detection zone is located at about 15 mm from the upstream end of a porous carrier (e.g. nitrocellulose membrane) and a capture zone is located at about 8 mm from the upstream end of a porous carrier (e.g. nitrocellulose membrane). A reagent zone may be provided on a separate porous carrier, located upstream of a porous carrier comprising a capture zone and a detection zone. There is no inherent limitation on spacing between a capture zone and the detection zone. However, in embodiments in which the assay device is designed to be read visually by a user, the capture zone will be spaced sufficiently far away from the detection zone so that it is not visible to a user observing the detection zone. As such, the dimensions of an observation window for observing the detection zone, and position of the detection zone below the window may be factors in determining the most suitable position for the capture zone.

Sample

Whilst urine is preferred as a sample matrix for home pregnancy testing the sample may be any suitable body fluid, such as whole blood, plasma, serum or urine. A urine sample is strongly preferred as such a sample is readily obtainable and does not require an intrusive procedure to be performed. In addition, use of urine sample facilitates self-testing by a user. Other samples may be collected using a swab, sanitary towel, bandage and the like and applied directly to the device followed by an elution buffer to help mobilize the sample components along the flow path. The sample may be collected as described above and placed into an elution buffer prior to this being applied to the test device.

Elapsed Time and Reader Properties

The outcome of the test may be determined by visual inspection of the detection zone by a user, usually following a set period of time following application of sample to the device, or on the development and visual appearance of a control line or other end of test indicator.

In the case of digital assay devices generally speaking, the test result will be determined after a particular time (tE) has elapsed (usually, but not necessarily, determined by reference to the time at which the sample was contacted with a sampling region of the assay device). If an assay result reading device is provided, this may comprise some sort of integral timing means in order to determine when tE is reached. The timing means may be actuated automatically by contacting the sample with the assay device (e.g. by the liquid sample allowing a current to flow), or may be triggered by the user (e.g. depressing a switch or the like) or by any other convenient means. The assay reaction may conveniently have reached equilibrium at tE but this is not essential.

The reader may make one or more measurement of the analyte signal at detection zone ahead of tE. Such early measurement of the signal at the detection zone can be used to output an end result to the user ahead of tE in the case where the signal at the detection zone is greater than a first threshold which indicates that the signal at the detection zone will be higher than the threshold set for a positive result at tE. Likewise if the signal at the detection zone is below a set threshold at any stage ahead of tE an early negative result could be output to the user ahead of tE.

The tE end point may conveniently be determined by the reader by reference to a particular time point (i.e. tE may be considered to occur a particular amount of time after commencement of the assay e.g. a particular interval after activation of the reader and/or insertion of an assay device into the reader and/or application of the sample to the assay device).

Housing

In a preferred embodiment, the assay device comprises a housing, which accommodates most or all of the functional components of the assays and the assay reagents. The housing is conveniently formed of a waterproof, synthetic plastics material and is preferably substantially opaque. An opacifier may be added to the plastics material in order to achieve a desired level of opacity. Suitable synthetic plastics materials for forming the housing include, in particular, polycarbonate, polystyrene, copolymers of polystyrene, polyolefins, polypropylene, polyethylene, and acrylonitrile. The housing may desirably be formed in two or more parts, which are joined together with the majority (or all) of the rest of the assay device components accommodated within or between the assembled parts of the housing. The parts of the housing may be joined and fastened by conventional fastening means, such as a snap fit action, or by plastic welding or the like.

In a preferred embodiment, the assay device comprises a housing, (typically having the features noted above), and wherein a sample application portion or zone extends beyond the housing, to facilitate application of a urine sample to the sample application portion or zone. The sample application portion or zone which extends beyond the housing may be covered, prior to use, by a removable cap. The cap may also preferably be formed of a synthetic plastics material, which may be opaque, or transparent or translucent. Typically the cap is replaced once sample has been applied to the sample application zone.

The housing may include a test window above the detection zone facilitating observation of the detection zone. The housing may obscure a user's view of the or each capture zone.

In another example a housing is not provided. In such an embodiment, the assay device components can be mounted on a support material such as Mylar to form what is typically known as a test strip. In this instance the capture line(s) may be obscured to the user by an opaque overlay attached or otherwise applied to cover the area of the capture zone(s). In other instances, utilizing such a test strip the capture zone(s) may be visible to the user, the user being instructed only to interpret the outcome of the result by observing the detection zone. Such test strip configurations not comprising a housing may also be read by a reading means as described herein.

Other Features

The assay device may conveniently comprise other features known to those skilled in the art and commonplace in conventional self-test or home test pregnancy testing devices, including (but not limited to), sample sufficiency indicator (e.g. as described in WO 2015/082646), an "anti-flood" pad (e.g. as disclosed in WO2012/069610), using flow of sample as an assay control (e.g. as disclosed in EP 1,484,611; U.S. Pat. No. 6,194,222); "early" determination of positive or negative results (e.g. as disclosed in EP 1,484,613; U.S. Pat. No. 5,679,584); automatic "wake up" of electronic devices (e.g. automatic actuation upon wetting of the device by sample, which completes an electrical circuit); and use of a digital assay progress meter (e.g. as in European Community Design Registration No. 1367304) or a "colour change wick" or the like which gives a visual indication to a user when sample has been applied to the test device and/or a visual indication that the assay has commenced (e.g. WO 2003/058245). The test device will advantageously be presented to the consumer in waterproof packaging, the packaging optionally further comprising a desiccant, such as a sachet of silica gel.

The assay flow path may conveniently be supported on some sort of support or backing layer to provide mechanical strength and a suitable degree of rigidity. The assay plus support may conveniently be referred to, and provided, as a test strip being used without a housing or indeed placed in a housing as described herein to form what is typically known as a test stick. The test stick or sticks may be adapted and configured to be inserted by the user into the test device, or the test stick or sticks may, more preferably, form an integral part of the test device which is purchased by a consumer with the test stick(s) pre-inserted or loaded in the test device.

Reader

In a preferred embodiment, the assay result may be directly read by a user, in the manner known from conventional 'self-test' pregnancy tests e.g. by a user inspecting one or more windows overlying the detection zone to determine the presence or absence of a detectable signal. In such embodiments, the assay device preferably does not include an assay reader. In an embodiment, the assay device of the invention is not configured to be read by an assay reader. Typically, in such user-read devices, the user will directly inspect the detection zone of the lateral flow or microfluidics assays. In other formats a user may determine the result at the detection zone by reference to a colour chart or indicator. Conveniently, the assay device may be provided together with instructions or guidance for reading the assay result (if the device does not interpret the assay results for the user). For example, the user may be provided with a printed colour chart to facilitate interpretation of such directly-read visual tests.

Alternatively, the detection zone may be read by an assay result reading means known as the assay result reader. In this case, the assay result reader is preferably configured to read the detection zone only and is not configured to read or analyse any capture zone present in the assay device. The assay result reader may be extrinsic to the assay device or integrated with the assay device. The assay result reader may advantageously comprise an electronic component, especially a digital electronic component, such as a microprocessor. The detection zone may be determined by optical means i.e. measuring the amount of light reflected and/or transmitted by the detection zone, in which an optically labelled reagent tends to accumulate in a manner proportional (directly or inversely) to the concentration of analyte in the sample. Alternatively, the detection zone may be read by, for example, magnetic or electrochemical measurement. Obviously, the way in which the assay is read may depend on the properties of the label(s) used to label the assay reagent(s). The data generated could be processed by an integral micro-processor and the test result output on the device itself via a LCD screen for example or be remotely transferred to an external device such as a mobile phone for processing in situ or transferred via a network connection to a central processing server. The result may be reported on the mobile phone or some other network connected device.

An extrinsic assay result reading means may comprise a dedicated result reading device (e.g. similar to that described in EP 1066530). Alternatively, an extrinsic assay result reader may be "non-dedicated", such as a mobile phone or other portable electronic device (e.g. a tablet computer), preferably provided with a camera, where the assay result is read by measuring the signal intensity generated by a label at the detection zone.

The assay result reader, whether extrinsic or forming part of an integrated assay device/assay result reader, may read and interpret the assay data, or may transmit assay data comprising running characteristics of the device such as flow times and various outputs from the measurement system to a remotely-located device for the assay data to be interpreted and the result obtained. The assay data may be transmitted to the remotely-located device in real time. The data may be transmitted via an internet connection, or may be stored on a memory device (such as a 'flash' drive or the like) which is physically transported to the remote device, or the data may be transmitted by wireless communication means (e.g. Bluetooth, near field communication [NFC], or the like).

A microprocessor may control the operation of the optical reading or other assay reading components, and will conveniently be programmed with, or be able to access, relevant assay signal threshold values for each of the analytes, compare the actual assay signal values with the predetermined thresholds, and interpret the assay results so as to determine the outcome of the pregnancy test.

The assay device may also comprise an assay result display, for displaying the outcome of the assay to a user. Typically the display will comprise an LCD, but other types of display are possible (e.g. using "electronic inks"). In those embodiments in which the assay device (or, more specifically, a component thereof) requires a power source to operate, then the assay device will preferably be provided with an integral power source, such as a battery. Very small, and cheap, batteries are commercially readily available. The device may also be provided with a switch to connect the integral power source and activate the device.

A combined pregnancy test stick/assay result reader device with display may be referred to as a "digital pregnancy test", and such digital test devices are commercially available and could be adapted, with the benefit of the present disclosure, to provide an assay device in accordance with the present invention.

The microprocessor will desirably be programmed so as to cause the assay result reading components to read the results of the assay(s); interpret the assay results; and display the conclusion to the user.

The components for reading the results of the assays will preferably comprise at least one light source, and at least one photodetector. The at least one light source is preferably a light emitting diode (LED). The at least one photodetector is preferably a photodiode or a phototransistor. The light source illuminates a detection zone on the assay, which zone tends to accumulate a labelled substance during performance of the assay, in a manner which depends on the concentration of the analyte of interest in the sample applied to the assay.

The device may typically utilize a reference zone—this is a portion of a microfluidics or lateral flow assay flow path which is used to reference a reading obtained from a detection zone. The use of a reference zone is well known to those skilled in the art helping account for unbound labelled reagent which may be on the flow path and/or the background coloration of the flow path by the test sample.

In one embodiment, light sources emit light of different wavelengths at different times, and the photodetector(s) distinguish the different wavelengths. Additionally, or alternatively, optical baffles (fixed or adjustable) may be used to control the area illuminated by a particular light source. More details of the sort of optical arrangements that can be used are disclosed in, e.g. EP 1,484,601, U.S. Pat. Nos. 6,055,060 and 5,889,585. For the avoidance of doubt, the term "light" as used herein is not intended to refer solely to radiation in that part of the electromagnetic spectrum which is visible to a human observer and encompasses, for example, ultra violet and infra-red radiation. Nevertheless, operation of the components in, and sensitivity to, the visible part of the spectrum may be preferred, and be selected according to the labelled reagent being used.

The microprocessor or computerised control means may comprise one or more of stored analyte threshold values, against which the assay result can be compared, to allow the assay result reading device to interpret the result and display an appropriate conclusion (e.g. pregnant or not pregnant) to a user. The microprocessor or control means can be programmed with an algorithm to measure the assay result, compare it with predetermined thresholds, and display the conclusion.

Control

In some embodiments it will be desirable for the test device also to comprise some sort of control function. This is conventional in self-test devices to provide some indication that the test has functioned correctly.

Typically a control function will comprise the use of a control zone, in which a labelled reagent will tend to accumulate if enough sample has been applied to the sample application zone of the assay device. Conventionally the labelled reagent will be a labelled antibody or other reagent which is releasably deposited in dried form at an upstream or proximal portion of a test strip, for example in the reagent zone, and is mobilized upon rehydration by the sample, and captured by a capture agent immobilised in the control zone. The control indicates whether enough sample has been applied to the test device and indicates that the test reagents have retained their binding properties to a reasonable extent, and that the labelled reagent has been mobilized to a sufficient extent. The labelled reagent used to form the control zone may be a second population of reagent to the first population of labelled reagent used in the detection of the analyte. A mixture of labelled reagent used in the detection of the analyte and a separate population of labelled reagent used to form the control zone may be used, both populations being involved in the formation of the control zone.

Embodiments described in relation to each aspect of the invention are as for each of the other aspects mutatis mutandis. Documents cited here are incorporated by reference to the fullest extent permitted by law. The prior art documents mentioned herein are incorporated to the fullest extent permitted by law.

The various features of the invention will now be further described by way of illustrative examples and by reference to the accompanying figures, in which:

FIG. 1A shows an embodiment of an assay device (100) for detecting the presence of an analyte (101) in a sample. The assay device comprises a sample application zone (102), a reagent zone (104) downstream of the sample application zone, a capture zone (110) downstream of the reagent zone, a detection zone (108) downstream of the capture zone, a control zone (109) downstream of the detection zone, and a sink pad (105) downstream of the control zone. When sample is applied to the sample application zone (102), it flows along a flow path of the assay device in the direction indicated by arrow (103).

The reagent zone (104) comprises a test mobilisable labelled conjugate (106) and control mobilisable labelled conjugate (107). The test mobilisable labelled conjugate (106) comprises a label (114) which is conjugated to binding reagent (113) (for example an antibody), which binds the analyte (101) or a first negative marker (112). The control mobilisable labelled conjugate (107) comprises a label (114) conjugated to a binding member that is bound by an immobilised binding member (116) at the control zone (109). The test mobilizable labelled conjugate may also function as a control conjugate.

The capture zone (110) comprises an immobilised capture species (115) (for example, an immobilised antibody) that is specific for the first negative marker (112).

The detection zone (108) comprises an immobilised binding reagent (111) (for example, an immobilised antibody), that is specific for the analyte (101).

A test window (117) is provided in assay device casing (not shown) above the detection zone (108) and control zone (109) such that the detection zone (108) and control zone (109) can be viewed by a user or read by an assay reader. The capture zone (110) is not visible through the test window (117) and is obscured by the assay device casing.

Figure 1B:
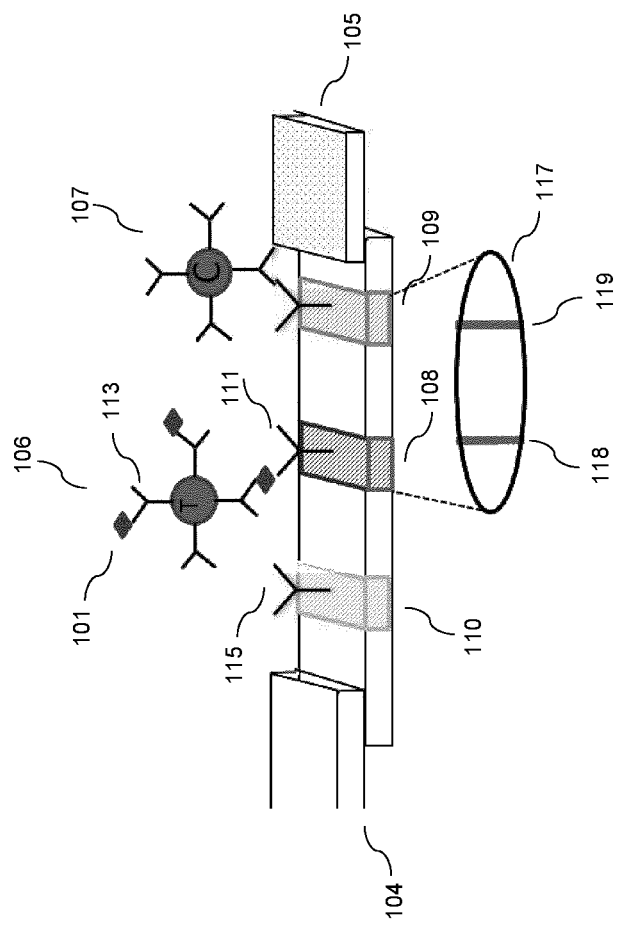

FIG. 1B shows how a positive assay result is obtained by the assay device shown in FIG. 1A. In this instance, the analyte (101) is present in the sample, but the first negative marker (112) is not present in the sample. The test mobilisable labelled conjugate (106) and control mobilisable labelled conjugate (107) are mobilised by the sample and flow downstream from the reagent zone (104). The analyte (101) is bound by the binding reagent (113) of the test mobilizable labelled conjugate (106) thereby forming a complex. The complex is not captured at the capture zone (110) because the immobilised capture species (115) at the capture zone (110) is specific for the first negative marker (112) and no first negative marker is present in the sample. The immobilised binding reagent (111) in the detection zone (108) binds the analyte in the complex, thereby capturing the complex. The control mobilizable labelled conjugate (107) is bound at the control zone (109). This results in the formation of a test line signal (118) and control line signal (119), both of which are viewable through the test window (117), indicating a positive result.

Figure 1C:
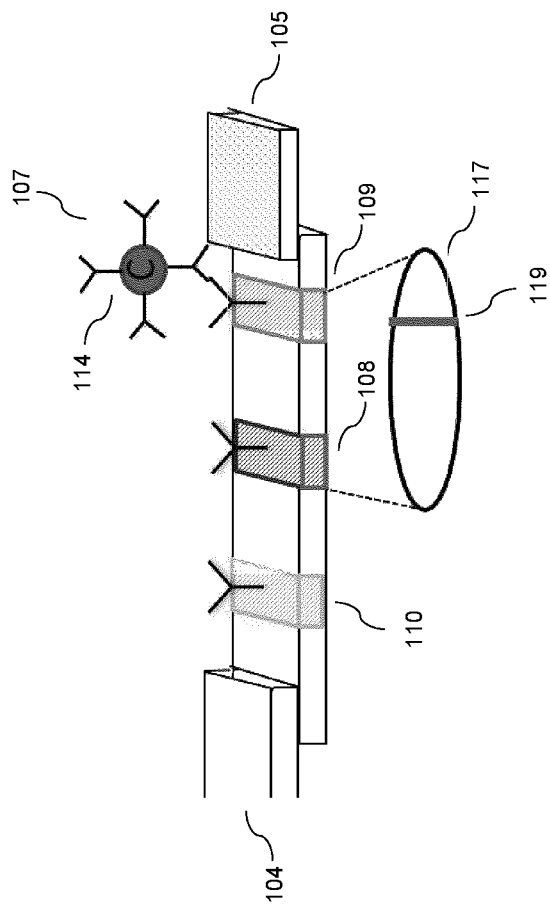

FIG. 1C shows how a negative result is obtained by the assay device of FIG. 1A when the analyte (101) and first negative marker (112) are absent from the sample. The control mobilisable labelled conjugate (107) is mobilised by the sample, flows downstream from the reagent zone (104) and is bound at the control zone (109). The test mobilisable labelled conjugate (106) is mobilised by the sample but is not able to bind at the detection zone (108) due to the absence of the analyte (101). This results in only a control line signal (119) developing and being viewable by a user at the test window (117), indicating a negative result.

Figure 1D:
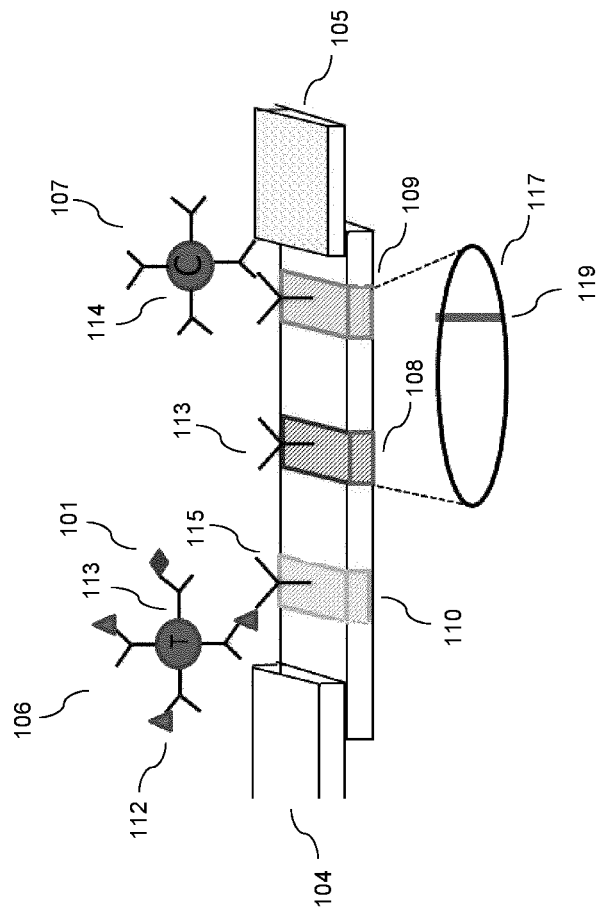

FIG. 1D shows how a negative result is obtained by the assay device of FIG. 1A when the analyte (101) and first negative marker (112) are present in the sample. The test mobilisable labelled conjugate (106) and control mobilisable labelled conjugate (107) are mobilised by the sample and flow downstream from the reagent zone (104). The first negative marker (112) and analyte (101) are bound by the binding reagent (113) of the test mobilisable labelled conjugate (106) to form a complex. The immobilised capture species (115) in the capture zone binds the first negative marker (112) of the complex, causing the complex to be captured at the capture zone (110). As the capture zone (110) is upstream of the detection zone (108), the test mobilisable labelled conjugate (106) is sequestered before it reaches the detection zone (108). Therefore, despite the presence of analyte (101) in the sample, the test mobilisable labelled conjugate (106) does not accumulate at the detection zone (108) in sufficient quantities to give a positive result. The control mobilisable labelled conjugate (107) is mobilised by the sample and bound at the control zone (109). This results in only a control line (119) being viewable by the user at the test window (117), indicating a negative result. The capture zone (110) is obscured from view.

Figure 2:
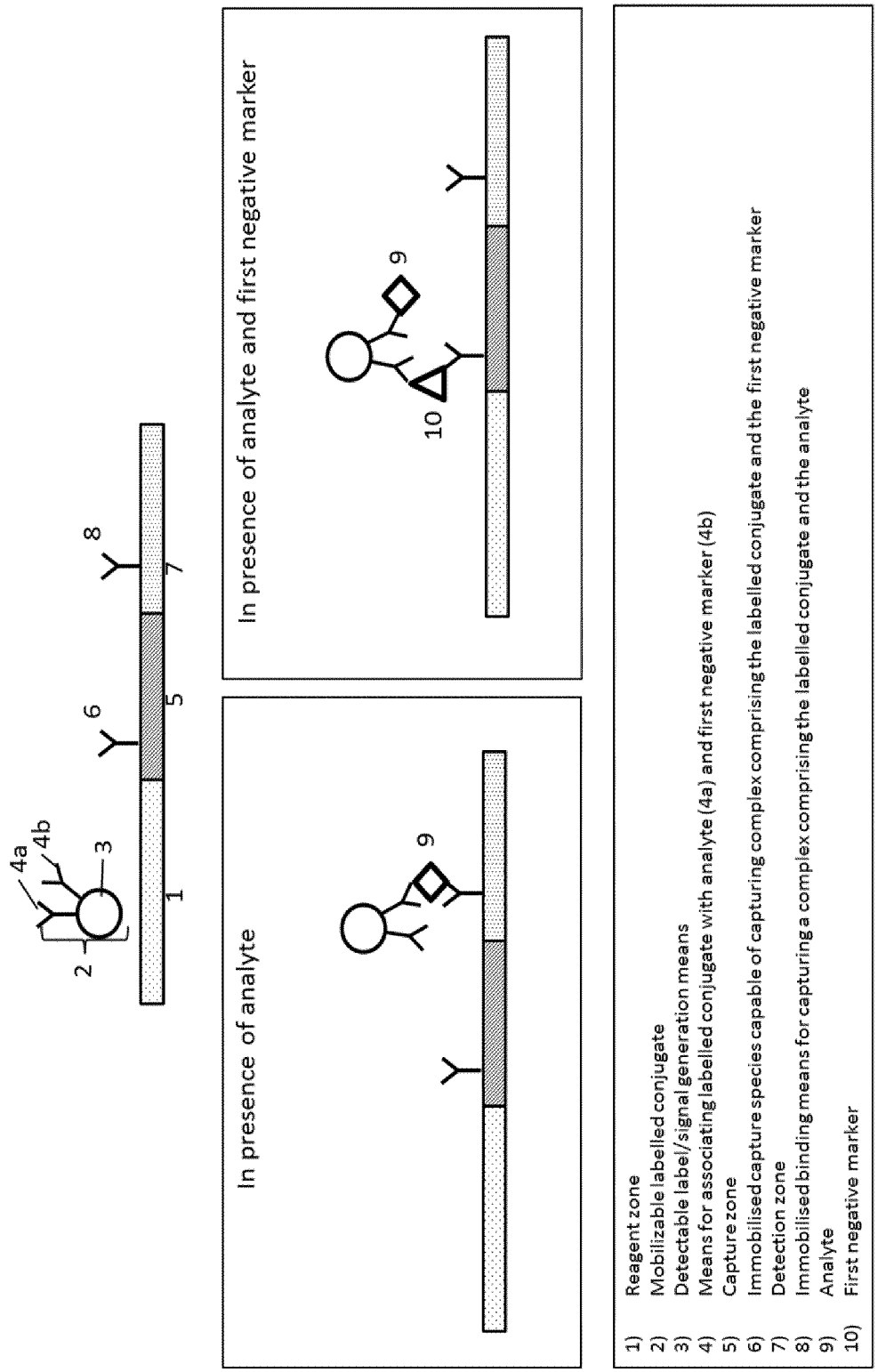

FIG. 2 shows a simplified schematic of an assay device of the type shown in FIG. 1. The assay device comprises a reagent zone (1), capture zone (5) downstream of the reagent zone (1), and detection zone (7) downstream of the capture zone (5). The reagent zone (1) comprises mobilizable labelled conjugate (2), which comprises detectable label (3) and means for associating the labelled conjugate with analyte (4a) and means for associating the labeled conjugate with first negative marker (4b). The capture zone (5) comprises immobilised capture species (6), which is capable of capturing a complex comprising the labelled conjugate (2) and first negative marker (10). The detection zone (7) comprises immobilised binding means (8) for capturing a complex comprising the labelled conjugate (2) and the analyte (9). In the presence of analyte (9) and the absence of first negative marker (10) (left panel), the means for associating the labelled conjugate with the analyte (4a) binds the analyte such that a complex is formed. This complex is captured at the detection zone (7) because the immobilised binding means (8) at the detection zone (7) binds the analyte (9) of the complex. In the presence of the analyte (9) and first negative marker (10) (right panel), the means for associating the labelled conjugate with the analyte (4a) binds the analyte (9) and the means for associating the labelled conjugate with first negative marker (4b) binds the first negative marker (10). It should be noted that, in this embodiment, the means for associating the labelled conjugate with the analyte (4a) and the means for associating the labelled conjugate first negative marker (4b) are different (e.g. different antibodies). However, they could be identical, e.g. identical antibodies that bind both the analyte and the first negative marker. A complex comprising the labelled conjugate, analyte (9) and first negative marker (10) is formed. This complex is captured at the capture zone (5) because the immobilised capture species (6) binds the first negative marker (10) of the complex. In this assay device, the capture zone (5) is obscured from view and the detection zone (7) is visible to a user or readable by an assay reader.

Figure 3:
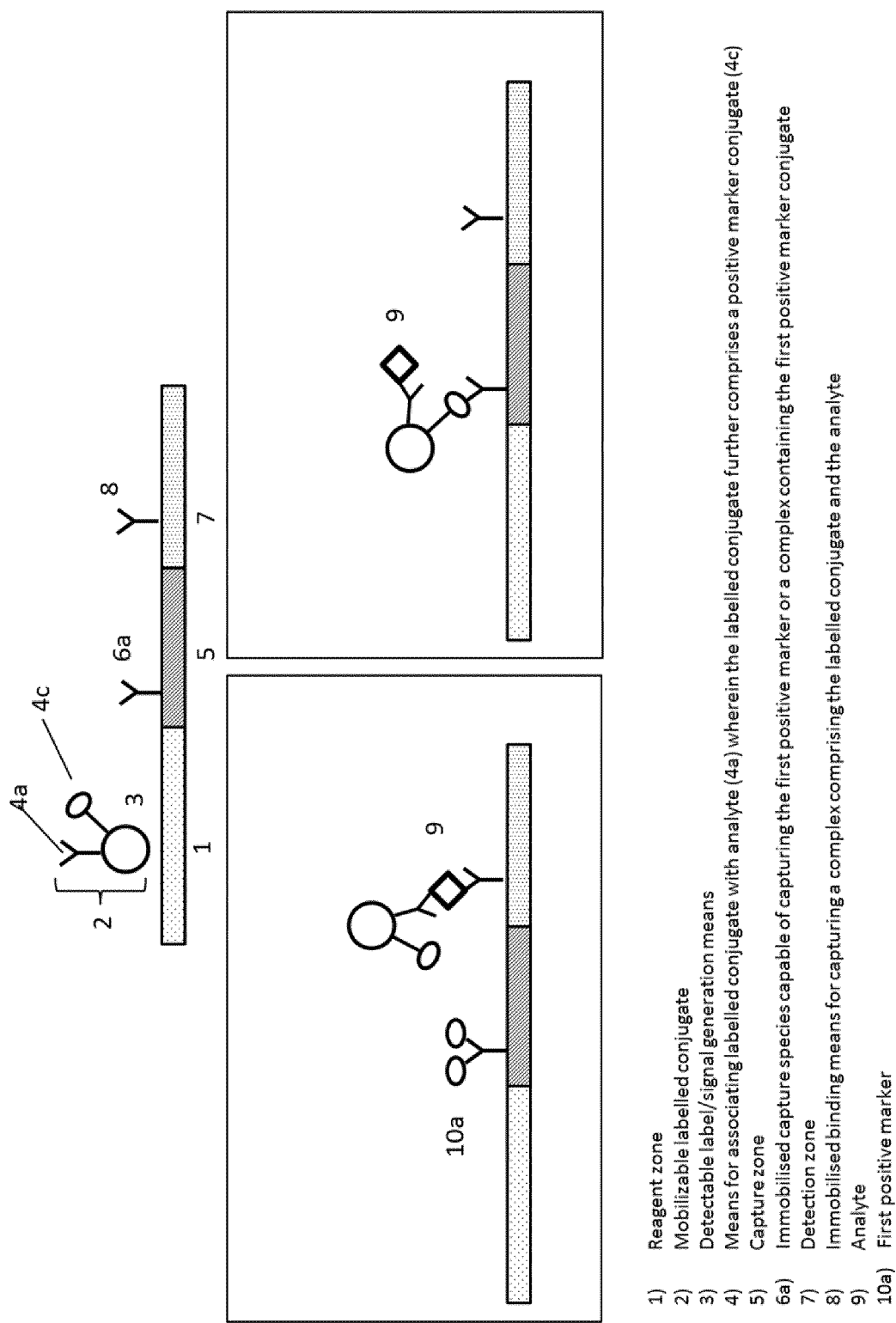

FIG. 3 shows a schematic of an assay device of the type shown in FIG. 2 except that (i) the mobilisable labelled conjugate (2) comprises a positive marker conjugate (4c) instead of means for associating the labelled conjugate with first negative marker (labelled (4b) in FIG. 2), and (ii) the capture zone (5) comprises immobilised capture species capable of capturing a first positive marker or a complex containing the positive marker conjugate (6a). In the presence of analyte (9) and first positive marker (10a) (left panel), the first positive marker (10a) is bound at the capture zone (5) by the immobilised species (6a) such that the labelled conjugate (2) cannot bind at the capture zone (5). The analyte (9) is bound by the means for associating the labeled conjugate with the analyte (4a) to form a complex. The complex passes through the capture zone (5) and is bound at the detection zone (7) because the immobilised binding means (8) at the detection zone (7) binds the analyte (9) of the complex. In the absence of the first positive marker (10a) and the presence of the analyte (9) (right panel), the analyte (9) is bound by the means for associating the labeled conjugate with the analyte (4a) to form a complex. The complex is bound at the capture zone (5) because the immobilised capture species (6a) at the capture zone (5) binds the positive marker conjugate (4c) of the complex.

Figure 4:
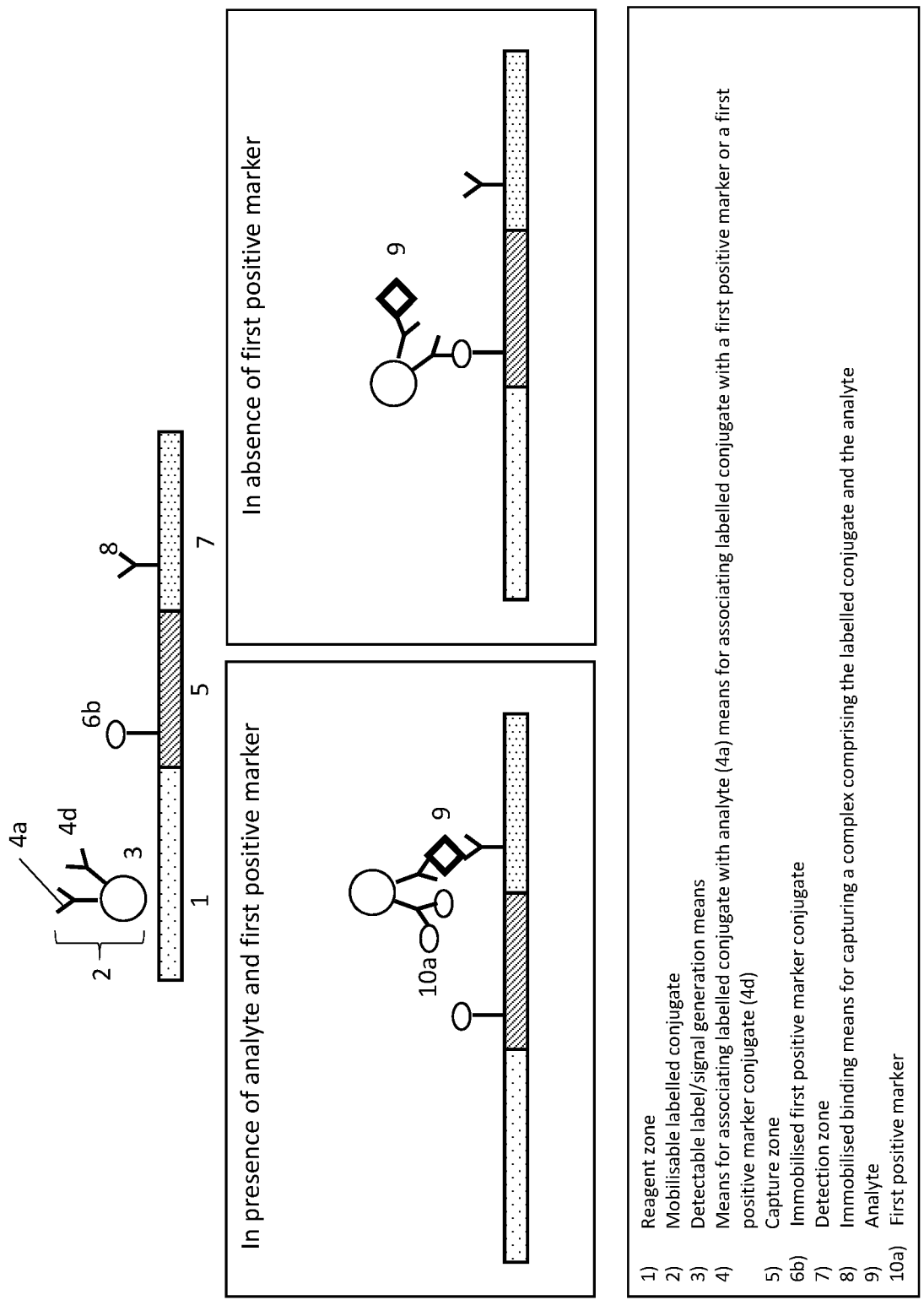

FIG. 4 shows a schematic of an assay device of the type shown in FIG. 3 except that (i) the mobilisable labelled conjugate (2) comprises means for associating the mobilisable labeled conjugate with first positive marker or first positive marker conjugate (4d) instead of positive marker conjugate ((4c) in FIG. 3), and (ii) the capture zone (5) comprises immobilised first positive marker conjugate (6b) instead of immobilised capture species capable of capturing the first positive marker or a complex containing the first positive marker conjugate (labelled (6a) in FIG. 3). In the presence of analyte (9) and first positive marker (10a) (left panel), the first positive marker (10a) is bound by the means for associating the mobilizable labeled conjugate with first positive marker or first positive marker conjugate 4(d) such that the labelled conjugate (2) cannot bind at the capture zone (5). The analyte (9) is bound by the means for associating the labeled conjugate with the analyte (4a) to form a complex. The complex passes through the capture zone (5) and is bound at the detection zone (7) because the immobilised binding means (8) at the detection zone (7) binds the analyte (9) of the complex. In the absence of the first positive marker (10a) and the presence of the analyte (9) (right panel), the analyte (9) is bound by the means for associating the labeled conjugate with the analyte (4a) to form a complex. The complex is bound at the capture zone (5) because the immobilised first positive marker conjugate (6b) is bound by the means for associating the mobilizable labeled conjugate with first positive marker or first positive marker conjugate (4d) of the labelled conjugate (2). It will be appreciated that the embodiments shown in the figures could be combined, such that, for example, both positive and negative markers influence the quantity of the labelled conjugate (and analyte when present in the sample) that reaches the detection zone and/or multiple negative and/or positive markers influence the quantity of labelled conjugate that reaches the detection zone. For example, a mobilisable labelled conjugate may comprise binding reagent for the analyte, first negative marker and a first positive marker, and a capture zone may comprise immobilised capture species for the first negative marker and an immobilised first positive marker conjugate. In another example, mobilisable labelled conjugate may comprise binding reagent for the analyte and first negative marker, and first positive marker conjugate, and a capture zone may comprise immobilised capture species for the first negative marker and an immobilised capture species for first positive marker and first positive marker conjugate.

Figure 5:
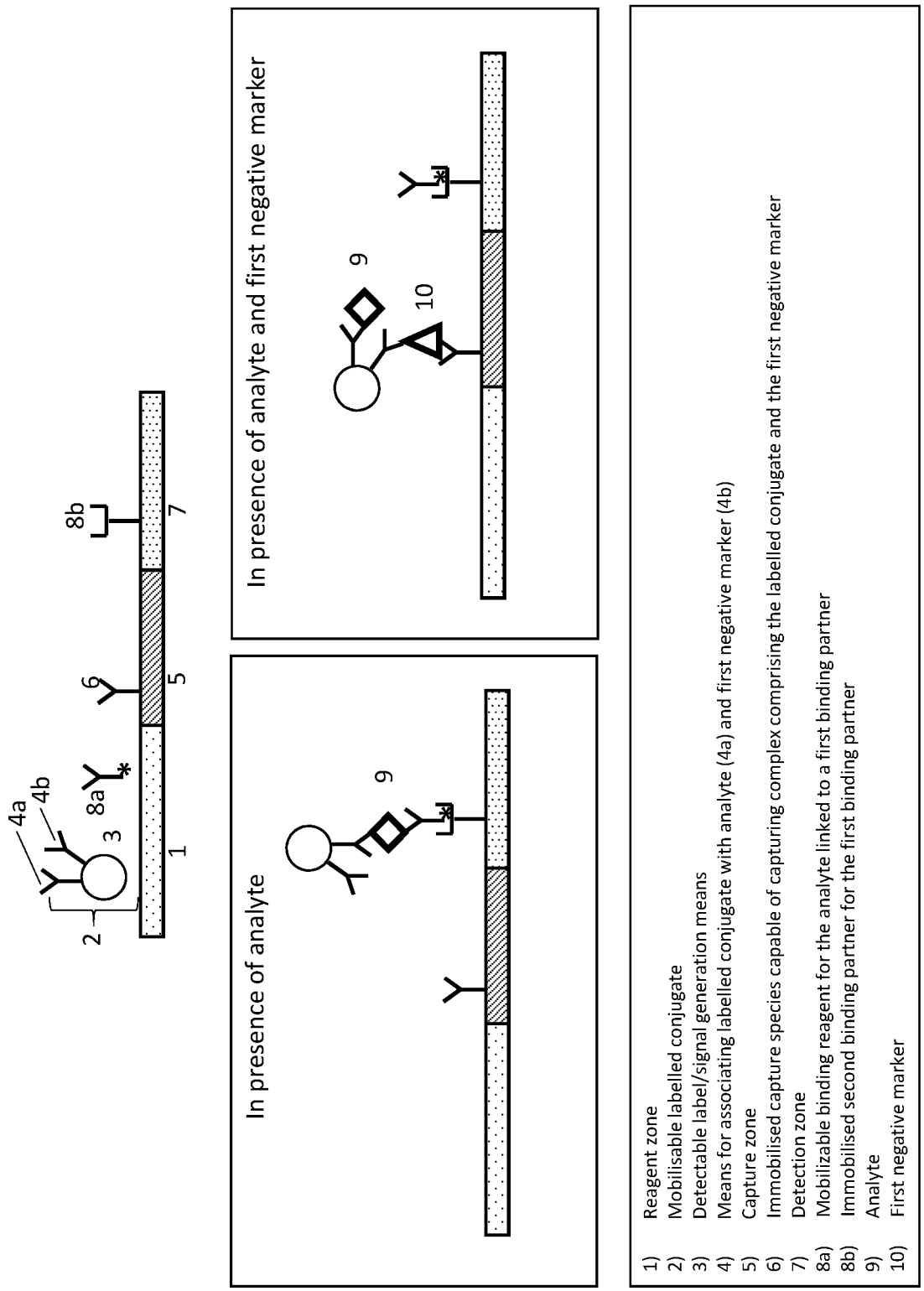

FIG. 5 shows indirect capture at the detection zone using a modified version of the device shown in FIG. 3. In this embodiment, the reagent zone (1) further comprises mobilisable binding reagent for the analyte linked to a first binding partner (8a). The detection zone (7) comprises immobilised second binding partner for the first binding partner (8b). In this way, mobilisable binding reagent for the analyte can be located at the detection zone (7) without being directly immobilised to the flow path.

In the presence of analyte (9) and the absence of first negative marker (10) (left panel), the means for associating the labelled conjugate with the analyte (4a) binds the analyte such that a complex is formed. The mobilisable binding reagent for the analyte linked to a first binding partner (8a) is mobilized and flows to the detection zone (7) where the first binding partner is bound by the second binding partner (8b). The complex is captured at the detection zone (7) by the mobilizable binding reagent for the analyte (8a) which is now located at the detection zone (7). In the presence of the analyte (9) and first negative marker (10) (right panel), the means for associating the labelled conjugate with the analyte (4a) binds the analyte (9) and the means for associating the labelled conjugate first negative marker (4b) binds the first negative marker (10). A complex comprising the labelled conjugate, analyte (9) and first negative marker (10) is formed. This complex is captured at the capture zone (5) because the immobilised capture species (6) binds the first negative marker (10) of the complex. The mobilisable binding reagent for the analyte linked to a first binding partner (8a) flows to the detection zone and is bound by the second binding partner (8b), but since the complex is captured at the capture zone (5) it is prevented from reaching the detection zone (7).

Figure 6:
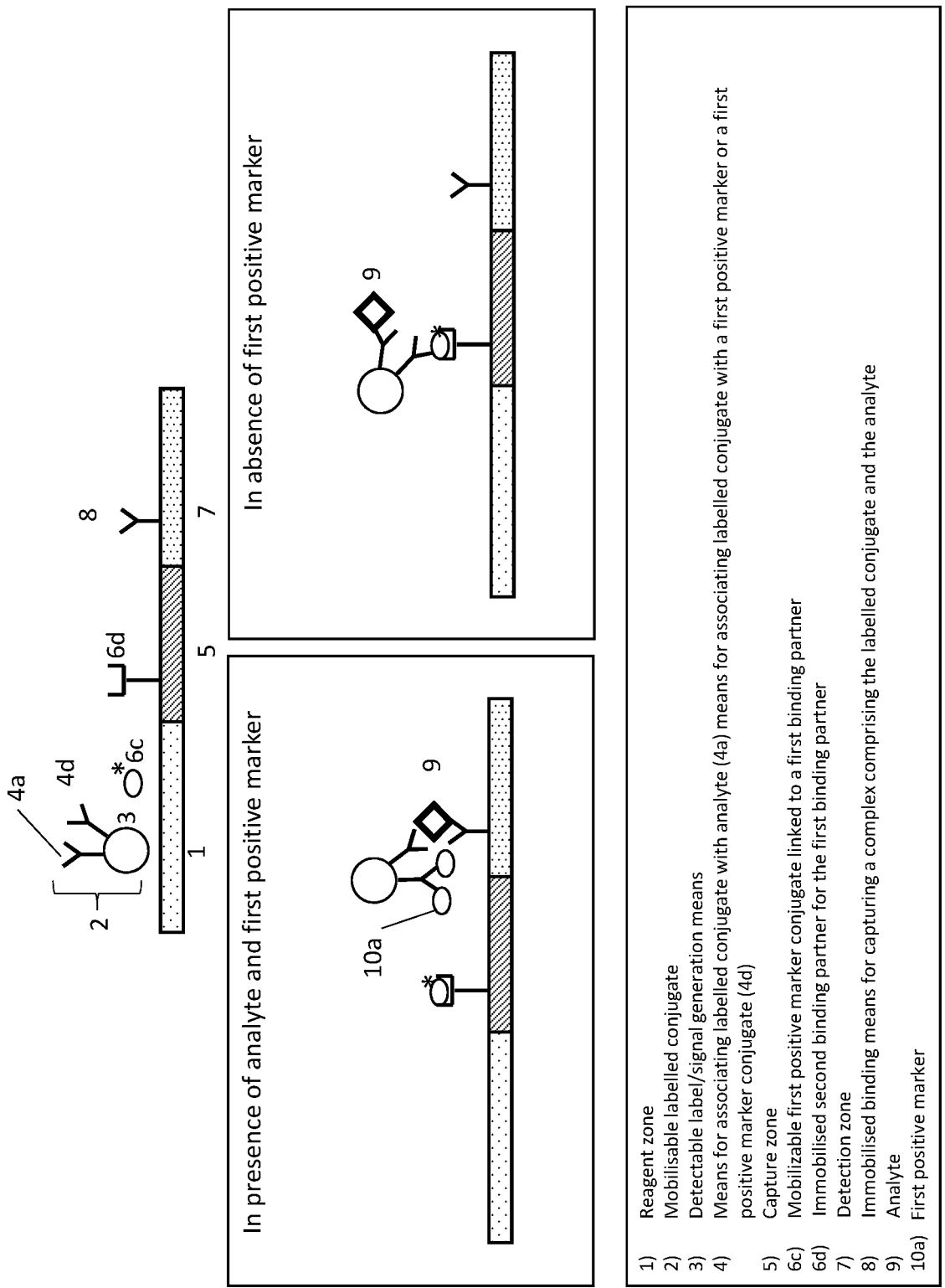

FIG. 6 shows a modified version of the of the device shown in FIG. 4. In this embodiment, the reagent zone (1) further comprises mobilizable first positive marker conjugate linked to a first binding partner (6c). The capture zone (5) comprises immobilised second binding partner for the first binding partner (6d). In this way, mobilisable first positive marker conjugate (6c) can be located at the capture zone (5) without being directly immobilised to the flow path.

In the presence of sample containing analyte (9) and first positive marker (10a) (left panel), the mobilizable first positive marker conjugate linked to a first binding partner (6c) is mobilized and flows to the capture zone (5) where the first binding partner is bound by the immobilised second binding partner (6d). The means for associating labelled conjugate with analyte (4a) of the mobilizable labelled conjugate (2) binds the analyte (9) to form a complex. The means for associating labelled conjugate with a first positive marker or a first positive marker conjugate (4d) of the mobilisable labelled conjugate (2) binds first positive marker (10a), preventing the complex from being captured by the first positive marker conjugate (6c), which is now located at the capture zone (5). The complex passes through the capture zone (5) and is bound at the detection zone (7) because the immobilised binding means (8) at the detection zone (7) binds the analyte (9) of the complex.

In the presence of the analyte (9) and absence of the first positive marker (10a) (right panel), the mobilizable first positive marker conjugate linked to a first binding partner (6c) is mobilized and flows to the capture zone (5) where the first binding partner is bound by the immobilised second binding partner (6d). The means for associating labelled conjugate with analyte (4a) of the mobilizable labelled conjugate (2) binds the analyte (9) to form a complex. The complex is bound at the capture zone (5) because the mobilisable first positive marker conjugate (6c), which is now located at the capture zone (5), is bound by the means for associating the mobilizable labeled conjugate with first positive marker or first positive marker conjugate (4d) of the labelled conjugate (2).

Figure 7:
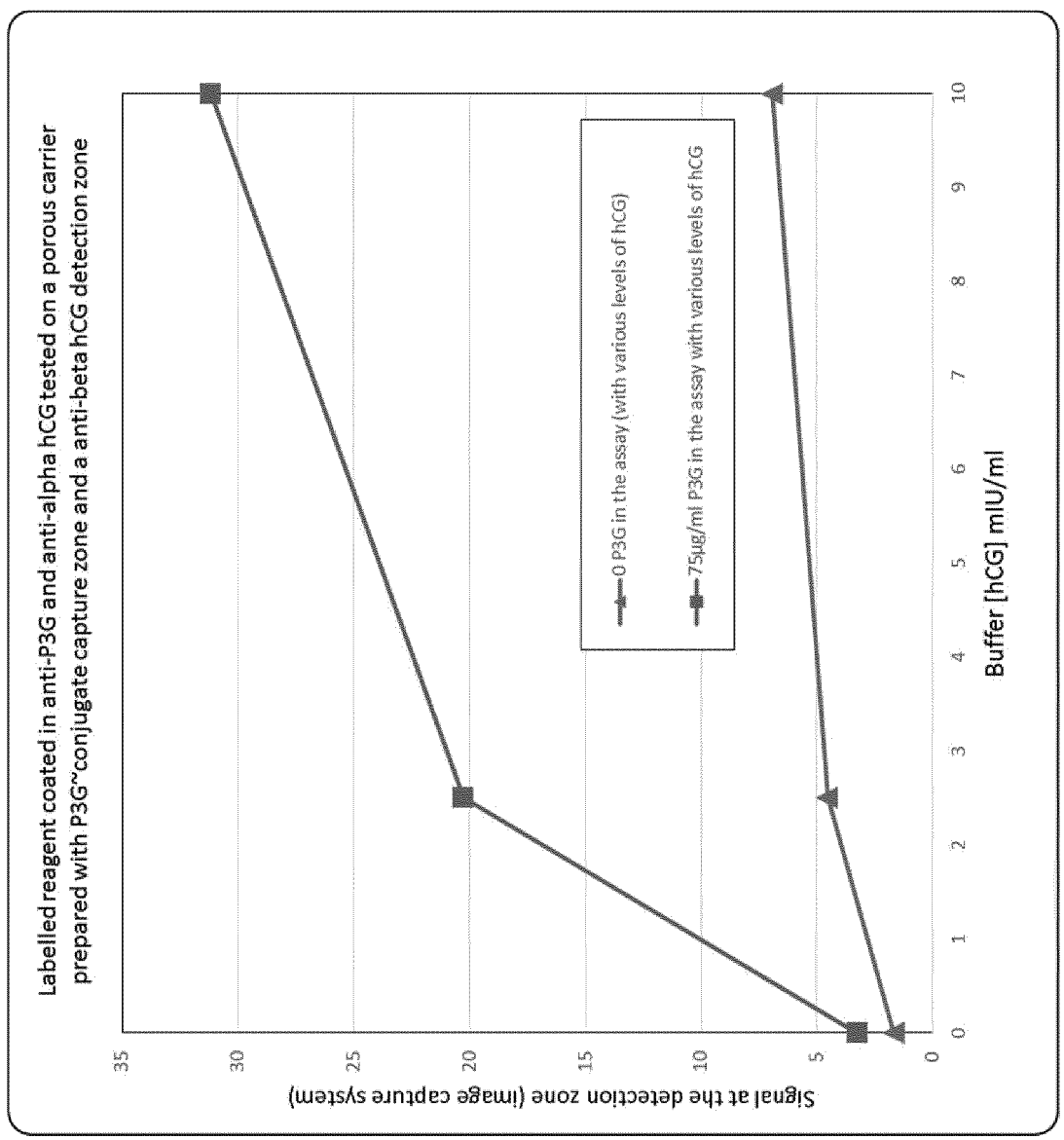

FIG. 7 is a graph showing the effect of P3G on the assay signal generated by labelled reagent coated in anti-P3G and anti-alpha hCG tested on a porous carrier prepared with a P3G_conjugate capture zone and an anti-beta hCG detection zone, over a range of hCG concentrations.

It should be noted that the positive marker conjugate shown in the figures could be replaced with a positive marker, for example if the positive marker is a non-hapten marker that does not require conjugation.

Figure 8:
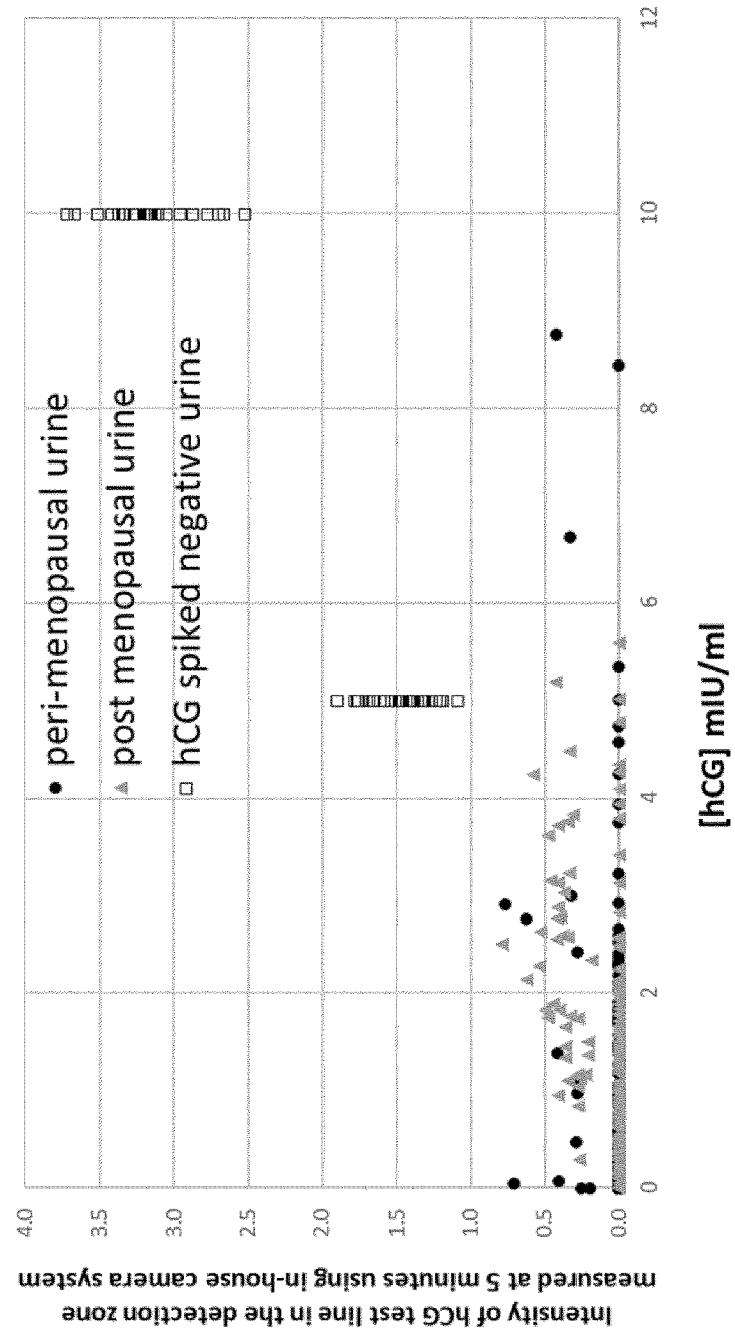
Figure 9:
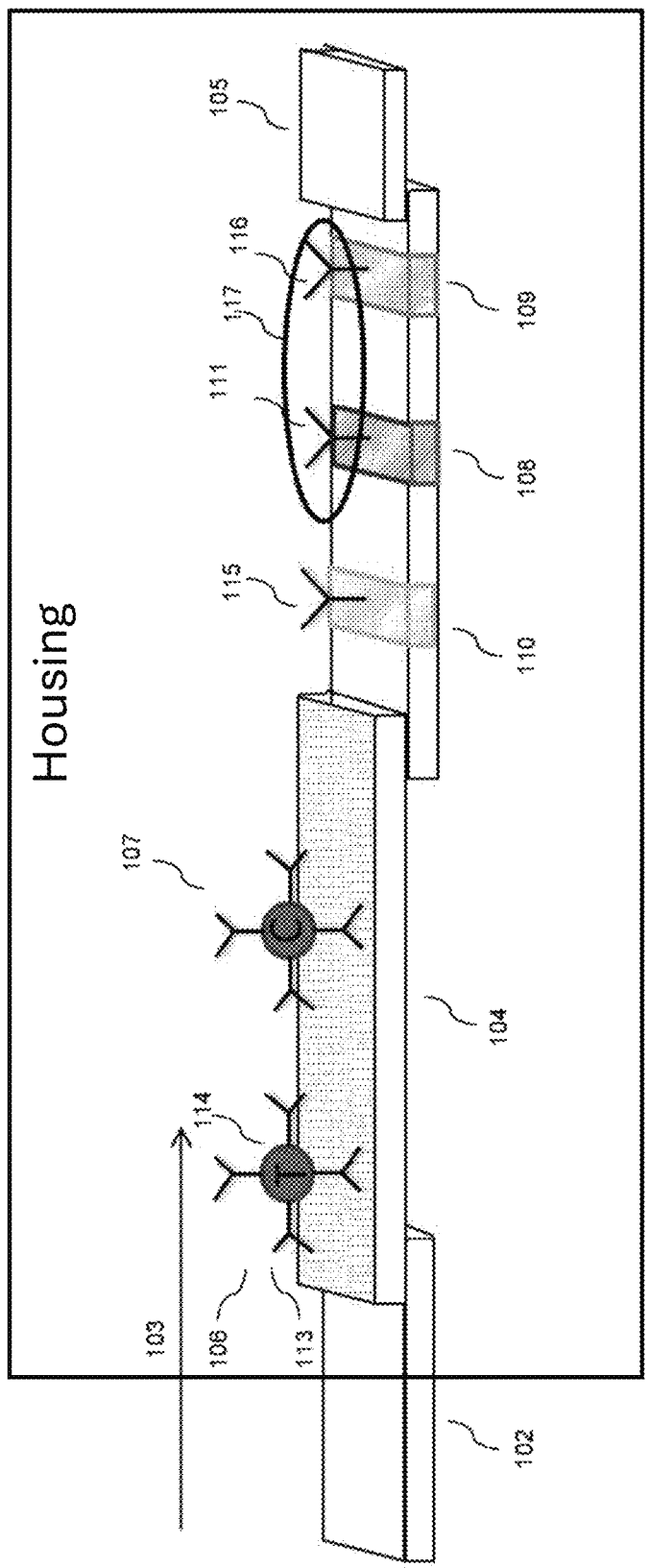

FIG. 8 is a block diagram showing an assay comprising a housing.

EXAMPLES

The invention will now be described with reference to the following non-limiting examples.

Example 1

This example describes the preparation of a pregnancy test strip with an anti-hCG detection zone and anti-FSH capture zones for use with clinical urine samples from pregnant and peri or post-menopausal women and spiked urine standards.

Production of Assay Reagents
Preparation of Gold Sol Labelled Antibody
Test Sol

A solution of mouse anti-alpha hCG antibody, 40 µg/mL, 40 mL, in 20 mM 2-(N-morpholino) ethanesulfonic acid (MES) buffer pH 6.5, was added to 40 mL of 40 nm gold sol at A520 nm=OD 5.0 (BBI International) and mixed rapidly with the gold sol on a magnetic stirrer at room temperature for 30 minutes. After 30 minutes 836.5 µL of a solution of 52.6 mg/mL beta casein solution in 50 mM carbonate buffer pH 10.5 was added to the reaction mixture and mixing was continued for a further 30 minutes at room temperature. The final concentration of beta casein in the reaction mixture was 0.55 mg/mL. The anti-alpha hCG antibody immobilised onto the gold sol is capable of binding both hCG and FSH through the alpha subunit of these hormones. The sol solution was poured into Falcon tubes (50 mL) and the solutions centrifuged (4000 rcf, 10 mins, 15° C.). The supernatants were carefully removed, wash buffer was added (1 mL, 10 mM MES pH 6.5 with 0.1 mg/mL beta casein) and the pelleted sol was vortexed and sonicated, to re-suspend. After resuspension the solutions were centrifuged (5000 rcf, 10 mins, 15° C.). The supernatant was removed and the sol was re-suspended in a small volume of storage buffer (10 mM MES pH 6.5 with 0.1 mg/mL beta casein). The final OD of the sol preparation was determined by measuring the absorbance at 520 nm.

Control Sol

A solution of Rabbit IgG antibody (Dako), 12.5 µg/mL, 20 mL, in 20 mM (4-(2-hydroxyethyl)-1-piperazineethanesulfonic acid) (HEPES) buffer pH 8.0, was added to 20 mL of 40 nm gold sol at A520 nm=OD 5.0 (BBI International) and mixed rapidly with the gold sol on a magnetic stirrer at room temperature for 30 minutes. After 30 minutes 76 µL of a solution of 52.6 mg/mL beta casein solution in 50 mM carbonate buffer pH 10.5 was added to the reaction mixture and mixing was continued for a further 30 minutes at room temperature. The final concentration of beta casein in the reaction mixture was 0.1 mg/mL. The sol solution was poured into Falcon tubes (50 mL) and the solutions centrifuged (4000 rcf, 10 mins, 15° C.). The supernatants were carefully removed, wash buffer was added (1 mL, 10 mM MES pH 6.5 with 0.1 mg/mL beta casein) to re-suspend the sol. and the pelleted sol was vortexed and sonicated, After resuspension the solutions were centrifuged (5000 rcf, 10 mins, 15° C.). The supernatant was removed and the sol was re-suspended in a small volume of storage buffer (10 mM MES pH 6.5 with 0.1 mg/mL beta casein). The final OD of the sol preparation was determined by measuring the absorbance at 520 nm.

Preparation and Means for Immobilising Gold Sol Labelled Binding Reagents

The anti-hCG coated gold sol (test) conjugate and the rabbit IgG coated gold sol (control) conjugate were spun down in a centrifuge and the supernatants removed. The resulting pellets were vortexed and sonicated and then reconstituted in a gold sol conjugate spray buffer to twice the desired OD of gold (in this example 16 OD/ml for the test sol and 10 OD/mL for the control sol). The test and control sols were then pooled 1:1 to give a spray solution containing 8 OD/ml test sol and 5 OD/ml control sol. The gold sol conjugate spray buffer used in the following examples contained 100 mM Tris pH 7.4, 20% w/v sucrose (Sigma) and 10% w/v bovine serum albumin (Proliant Biologicals SKU #68700). Glass fibre (GE Healthcare) was loaded onto a Biodot spray rig. The biodot spray rig was set up to impregnate/infuse the glass fibre with test and control conjugate at the desired location on the glass fibre (6.5 mm from the downstream edge). In this example the glass fibre was sprayed with a single pass of the OD10 conjugate with a plot rate of 1.7 uL/cm at a distance of 6.5 mm from the downstream edge of the glass fibre. In addition 0.56 M EDTA in water was sprayed at a plot rate of 1.7 ul/mm 16 mm from the downstream edge of the glass fibre. The gold sol infused glass fibre was dried at 55° C. and stored at room temperature with desiccant in sealed foil pouches.

Preparation and Means for Locating and Immobilising Specific Binding Substances

Mouse anti-beta hCG antibody was diluted in phosphate buffer with 0.05% (w/v) sodium azide (PBSA) to 3 mg/mL prior to immobilisation on nitrocellulose. Anti-beta FSH antibody was diluted in PBSA to 1.5 mg/mL prior to immobilisation on nitrocellulose. A Poly Vinyl Alcohol (PVA) blocking buffer (pH 9) was prepared (Tris base 20 mM (Sigma), PVA 1% w/v (PVA 80% hydrolysed, 9-10K MW Sigma), Tween 20 0.05% w/v (Sigma) and NaCl 150 mM (Sigma). A PVA blocking solution was prepared by addition of 2% w/v of sucrose (Sigma) and 2.5 mls of Ethanol (Sigma) to 47.5 mL of PVA blocking buffer. White backed nitrocellulose with pre-punched location holes to a pitch of 4 mm (MDI) was cut into 35 cm*40 mm bands. A Biodot plotter was set up to plot a single line of the anti-beta hCG antibody to form a detection zone and anti-beta FSH antibody to form a capture zone and goat anti rabbit (Lampire) to form a control zone in the desired locations on the nitrocellulose band. The anti-beta hCG antibody was deposited at a distance of 15 mm from the bottom (upstream end) of the nitrocellulose membrane at a concentration of 3 mg/ml and a plot rate of 1 uL/cm, the anti FSH antibody was deposited at a distance of 8 mm from the bottom (upstream end) of the nitrocellulose at a concentration of 3 mg/mL with a plot rate of 3 µL/cm and the goat anti rabbit antibody was deposited at 22 mm from the bottom (upstream end) of the nitrocellulose membrane at a concentration of 2 mg/mL and a plot rate of 1 uL/cm. After plotting, the bands were dried at 55° C., blocked using the PVA blocking solution and then dried at 65° C. and stored at room temperature with desiccant in sealed foil pouches.

Test Strip Construction

The assay components were assembled into a test strip with the aid of a kinematic universal laminator module assembly unit. Backing laminate (Lohman) was placed onto the kinematic card platen and a blocked nitrocellulose band with immobilised capture, detection and control zones was affixed to the backing laminate in a pre-determined position. A band of anti-alpha hCG and rabbit IgG gold sol conjugate infused glass fibre was affixed to the backing laminate with a 2 mm overlap over the nitrocellulose band. A roller mat ensured good contact of all the components of the strip with the backing laminate. The bands were then cut into 4 mm individual strips using an in-house rotary cutter and stored with desiccant in foil pouches until ready for use.

Device Preparation

Test strips were assembled into plastic case parts together with an absorbent sampler impregnated with a buffer to control pH. The case parts comprised a lower half with a location pin and an upper half with a window for viewing the lines on the nitrocellulose strip and a means to hold the absorbent sampler in contact with the assay strip upstream of the reagent zone. The window position was such that the test and control lines were visible to the user, but the capture zone lines were hidden. The strip was placed in the lower case part using the pin to locate the strip. A 4×12 mm sink pad (GE Healthcare) was placed at the proximal end of the strip. The top case was used to close the device.

Example 2

This example demonstrates an assay utilising a negative marker for pregnancy, (FSH) in combination with hCG, the analyte of interest. The impact of the negative marker on the sensitivity of the hCG assay is demonstrated by having a capture zone comprising anti-beta FSH antibody positioned upstream of an anti-beta hCG zone as the detection zone. The influence of the FSH capture zone on the number of labeled conjugate particles travelling to the detection zone as a function of the level of FSH in the sample could hence be determined.

Method

Devices were prepared as described in Example 1. In order to test the impact of FSH concentration on assay sensitivity, non-pregnant urine samples were collected from in-house volunteers. The urine was depleted using an anti-alpha TSH antibody to remove engodenous hCG and LH and then spiked with hCG and FSH at a range of concentrations. Devices were run by applying the spiked urine to the absorbent sampler of the assay device. The intensity of the line in the detection zone was measured at 5 minutes using an in-house camera system and devices were also scored as pregnant or not pregnant by 40 lay users. Lay users were non SPD staff, who had not previously seen this type of pregnancy test. Each lay user visually scored 7 devices, which were presented to them in a randomized order.

Results

As the concentration of FSH in the urine sample was increased both the camera-measured detection zone line intensity and the number of devices scored as pregnant by a lay user was reduced, demonstrating the impact of FSH as a negative marker on hCG assay sensitivity. The results are shown in Table 1 below.

TABLE 1

Mean line intensity measured by in-house camera system and number of devices scored visually positive for pregnancy test strips with anti-hCG detection zone and anti-FSH capture zone run with pooled negative urine spiked with hCG and FSH.

| [hCG] | Line intensity in detection zone [FSH] mIU/mL | | | No. devices scored pregnant by lay user [FSH] mIU/mL | | |
|---|---|---|---|---|---|---|
| mIU/ml | 0 | 30 | 100 | 0 | 30 | 100 |
| 3 | 1.28 | 0.43 | NT | 31/40 | 0/30 | NT |
| 10 | 3.77 | NT | 0.61 | 40/40 | NT | 3/40 |

NT—not tested

Example 3

This example demonstrates an assay utilising a negative marker for pregnancy, (FSH), in combination with the hCG, the analyte of interest, in clinical samples comprising pregnant urines and peri/post menopausal urines containing pituitary hCG.

Method

Devices were prepared as described in Example 1. In order to test the impact of the invention on the ability of the assay to distinguish between hCG derived from pregnancy and pituitary hCG, urine samples collected from pregnant and peri/post-menopausal women were used. 32 pregnant urines were selected that had been collected on day −5 to day −3 relative to the day of the expected period, with hCG concentration ranging from 3-22 mIU/mL. Fifty urine samples from peri and post-menopausal women containing 5-10 mIU/ml pituitary hCG were also selected for testing.

Devices were run by applying the urine to the absorbent sampler of the assay device. The intensity of the line in the detection zone was measured at 5 minutes using an in-house camera system and devices were also scored as pregnant or not-pregnant by three lay users (SPD staff who do not read devices as part of their job)

Results

As shown in Table 2 below, none of the 50 peri/post menopausal urines were called as pregnant, despite containing hCG up to a maximum concentration of 10 mIU/mL, whereas 90% of the pregnant urines were called as pregnant, including those with a hCG concentration as low as 3 mIU/ml. This demonstrates the effectiveness of the use of a capture zone for a negative marker in producing a sensitive pregnancy test which maintains high specificity for pregnancy in clinical samples.

TABLE 2

Number of devices scored as pregnant by lay users when run with peri/post menopausal urine samples containing 5-10 mIU/ml of hCG and pregnant urine samples from day −5 to day −3 relative to the expected period

| | Devices scored as pregnant |
|---|---|
| Peri/post menopausal urine | 0/50 |
| Pregnant urine | 29/32 |

Example 4

This example demonstrates an assay utilising a positive marker for pregnancy, (P3G), in combination with hCG, the analyte of interest. The impact of the positive marker on the sensitivity of the hCG assay is demonstrated by having a capture zone comprising P3G-conjugate positioned in a capture zone upstream of an anti-beta hCG zone as the detection zone. The impact of the P3G conjugate on the amount of particles travelling to the detection zone as a function of the level of P3G in the sample could hence be determined. Blue latex particles were coated in a mixture of anti-alpha hCG as well as anti-P3G by mixing the antibodies together prior to coating onto latex particles. On testing, the coated latex preparation was applied to a porous carrier in various mixtures of P3G (positive marker) and hCG (analyte of interest) to observe the impact that the level of P3G in the assay had on the signal seen at the detection zone.

Preparation of Labelled Reagent, (Latex Coated in Anti-Alpha hCG as Well as Anti-P3G)

1 ml latex, (400 nm in diameter) at 2% solids was washed by centrifugation, (13,000 rcf for 4 minutes at 20° C.), the supernatant was removed and the pellet resuspended into 500 µls of 100 mM borate buffer pH 8.5 to give a final concentration of 4% solids latex. The latex was heated at 46° C. for ~ 30 minutes with gentle mixing. A mixture coating 1200 µg/ml anti-alpha hCG, (mouse monoclonal) plus 600 µg/ml anti-P3G, (Fab, mouse monoclonal) was made in 100 mM borate buffer pH 8.5. The mixture of antibodies was heated at 46° C. for 30 minutes with gentle mixing.

The mixture of heated antibody was added to the heated latex in equal volumes and mixed to give 1 ml of latex at 2% solids plus 600 µg/ml anti-alpha hCG and 300 µg/ml anti-P3G. 100 µls 95% ethanol plus 0.5% sodium acetate was added to the mixture and the resulting mixture incubated at 46° C. for 60 minutes with gentle mixing.

The latex was blocked by the addition of 110 µls of 200 mg/ml BSA, (Proliant Biologicals, reagent grade) in deionized water, and mixed for 30 minutes at 46° C. Once blocked in BSA the latex was washed by three centrifugation steps with removal of the supernatant, (supernatant discarded), the pellet being re-suspended into 10 mM borate buffer pH 8.5 after each centrifugation step. The supernatant was removed following the final centrifugation step and the latex resuspended into 800 µls of buffer comprising 10% BSA and 20% sucrose in 100 mM Tris pH 8.5, (final suspension buffer) resulting in ~2% solids latex. The latex was further diluted 1+7 in final resuspension buffer prior to use.

Preparation of a Porous Carrier Comprising an Immobilised Zone of Anti-Beta hCG (Detection Zone and a P3G~Conjugate Immobilised Zone as a Capture Zone.

Nitrocellulose membrane, (MDI 12 µm) was used as a porous carrier onto which a capture zone and a separate detection zone were deposited.

Anti-beta hCG at 3 mg/ml in PBSA was applied as a zone, (detection zone) onto nitrocellulose membrane 10 mm from the proximal end of the test strip using the Biodot plotter as described in Example 1. P3G~conjugate having a protein concentration of 3 mg/ml (prepared by linking P3G to a mouse monoclonal antibody as a carrier protein) was deposited 5 mm from the proximal end of the test strip as a capture zone, upstream of the detection zone. Following a drying step, the membrane was blocked in PVA and dried prior to being stored in a foil bag with desiccant. The resulting membrane was cut into 4 mm wide test strips, each test strip having a capture zone 5 mm from the proximal end of the test strip and a detection zone 10 mm from the proximal end of the test strip.

Testing Latex Particles Coated in Anti-P3G as Well as Anti-Alpha hCG on a Porous Carrier Prepared with a Capture Zone of P3G~Conjugate and an Anti-Beta hCG Zone as a Detection Zone.

The testing procedure or "assay" involved making a mixture of coated latex plus buffer standard, (sample) containing various levels of P3G and hCG, (5 µls of diluted latex plus 50 µls of buffer standard) and applying this mixture to the nitrocellulose membrane comprising the capture and detection zones. This was achieved by dipping the proximal end of a test strip in a pool or mixture containing the coated latex and the buffer standard containing various levels of P3G and hCG. A paper sink material was applied at the distal end of the test strip, (~ 20 mm downstream of the detection zone) to act as a sink. Once the mixture at the base of the strip had run dry, the test strips were washed by applying buffer, (50 µls of PBSA plus 0.1% ovalbumin) to the base of the strips and allowing this to traverse through to the sink washing unbound latex to the distal end of the test strip. Once washed, the signal developed at the detection zone was measured on an optical reading, system (image capture system) and the intensity of the signal developed at the detection zone was reported as a numerical number, the higher the signal intensity at the detection zone the greater the numerical number.

In order to test the impact of the P3G assay on the response seen at the detection zone, the latex preparation was tested in buffer containing 0 µg/ml P3G but having various levels of hCG. This was repeated in buffer standards containing 75 µg/ml P3G but also containing various levels of hCG.

The latex preparations was mixed with buffer standards comprising 0 µg/ml P3G also containing various levels of hCG: 0, 2.5 and 10 mIU/ml hCG and the test strips having a capture zone of P3G~conjugate and an anti-beta hCG as a detection zone were held vertically whilst being dipped in the mixture allowing the mixture to move through the membrane into the sink applied at the distal end. The test strips were washed as described above and readings of the detection zone taken on an imaging system.

The above was repeated, this time with the latex preparation being mixed with buffer standards comprising 75 µg/ml P3G but also containing 0, 2.5 and 10 mIU/ml hCG. The procedure above was followed and readings of the detection zone taken on an in-house camera system.

Results

Latex tested with 0 µg/ml P3G in the assay caused a large proportion of the labelled reagent to be captured at the capture zone, (anti-P3G on the labelled reagent being bound to the P3G~conjugate at the capture zone). This significantly reduced the amount of labelled reagent travelling to the detection zone resulting in a reduced response to hCG seen at the detection zone. The presence of 75 µg/ml P3G in the assay reduced the capture of the labelled reagent at the capture zone, (due to the P3G in the buffer standard binding the anti-P3G on the labelled reagent preventing the labelled reagent binding to the P3G~conjugate zone) allowing more of the labelled reagent to travel to the detection zone where a significantly stronger signal was seen in the presence of hCG (see FIG. 7). Clearly the level of the positive marker in the assay influences the response generated to hCG at the detection zone, and this is dependent on the amount of positive marker (in this case P3G) in the assay.

Example 5

This example demonstrates an assay utilising a negative marker for pregnancy (FSH), in combination with hCG, the analyte of interest. The impact of the negative marker on the sensitivity of the hCG assay in clinical urine samples is demonstrated by having a capture zone comprising anti-beta FSH antibody positioned upstream of an anti-beta hCG zone as the detection zone. The impact of the FSH capture zone on the assay signal produced in the detection zone is shown using peri and post-menopausal clinical urine samples with physiological levels of hCG and FSH and for comparison with standards prepared by spiking hCG into an FSH and hCG depleted urine pool.

Method

Devices were prepared as described in Example 1. In order to test the impact of the negative marker on the sensitivity of the hCG assay in clinical samples testing was carried out using urine samples collected from peri/post-menopausal women. In addition, standards prepared by spiking known concentrations of hCG into an FSH & hCG depleted urine pool (depleted of FSH & hCG as described in Example 2). Two hundred peri-menopausal samples and two hundred post menopausal samples were tested. The level of hCG in these samples was measured by a clinical analyser, (DELFIA). In addition, 25 devices were run with 5 mIU/ml hCG spiked into hCG & FSH depleted pooled urine. A further 25 devices were run with 10 mIU/ml hCG spiked into hCG & FSH depleted pooled urine. Devices were run by applying the urine to the absorbent sampler of the assay device. The intensity of the hCG line in the detection zone was measured 5 minutes from the addition of the sample using an in-house camera system and devices were also visually scored as pregnant or not-pregnant by two technicians by observing the result at the hCG line as being a visible line, (indicating a positive, hence pregnant result) or the absence of a line, (indicating a negative, hence not pregnant result). The order in which clinical samples and standards were tested was randomised and the technicians reading the test were blinded to the randomisation to remove any technician reader bias.

Results

As shown in Table 3 below, 92% of devices run with 5 mIU/ml hCG spiked pooled urine, and 100% of devices run with 10 mIU/ml hCG spiked pooled urine were read visually as pregnant by the technicians. All 200 peri-menopausal and 200 post-menopausal urine samples were read visually as not pregnant by the two technician readers despite including hCG concentrations of up to 8.8 mIU/ml hCG. Such hCG levels seen in peri and post-menopausal urines would potentially give rise to a false positive result in a traditional pregnancy test designed to detect low levels of hCG as low as 5 mIU/ml.

TABLE 3 hCG concentration range and visual scoring of devices run with peri and post-menopausal urine samples and hCG standards prepared by spiking an FSH & hCG depleted negative urine pool

| | hCG conc (mIU/ml) | | visual score | | | |
|---|---|---|---|---|---|---|
| | Min | Max | not pregnant | | pregnant | |
| Peri menopausal urine | 0 | 8.76 | 200 | 100% | 0 | 0% |
| Post menopausal urine | 0 | 5.59 | 200 | 100% | 0 | 0% |
| 5 mIU/mL hCG spiked urine | 5 | 5 | 2 | 8% | 23 | 92% |
| 10 mIU/mL hCG spiked urine | 10 | 10 | 0 | 0% | 25 | 100% |

FIG. 8 shows the signal intensity of the hCG test line in the detection zone, measured by an in-house camera system, plotted against hCG concentration. For the spiked standards, where no FSH is present, signal intensity increases as hCG concentration increases. Regarding the peri and post-menopausal samples which contain hCG and FSH, clearly the presence of FSH in the samples reduces the quantity of label reaching the hCG test zone since the label becomes bound at the capture zone. This results in a reduced signal at the hCG detection zone and hence provides a true result at the hCG detection zone as being negative for pregnancy for these peri and post-menopausal samples.

The invention claimed is:

1. An assay device for detecting the presence of an analyte in a sample, the device comprising an assay flow path, the flow path comprising:
   (a) a reagent zone comprising a mobilisable labelled conjugate comprising a detectable label directly or indirectly linked to
       means for associating the labelled conjugate with the analyte and means for associating the labelled conjugate with a first negative marker which may be present in the sample;
   (b) one or more capture zones, wherein
       at least one capture zone comprises an immobilised capture species configured to capture a complex comprising the labelled conjugate and the first negative marker wherein capture of the complex is achieved by a specific binding reaction with first negative marker; and
   (c) a detection zone comprising immobilised binding reagent for capturing a complex comprising the labelled conjugate and the analyte, wherein the one or more capture zones is downstream of the reagent zone, and the detection zone is downstream of the one or more capture zones.

2. The assay device of claim 1, wherein the device is arranged such that, in use, the one or more capture zones is not visible to a user, and/or the device comprises a housing that obscures a user's view of the one or more capture zones, and/or the one or more capture zones is not readable by an assay reading means.

3. The assay device of claim 1, wherein the means for associating the labelled conjugate with the analyte comprises a binding reagent that binds an epitope of the analyte and/or an epitope that is shared by the first negative marker and the analyte.

4. The assay device of claim 1, wherein the means for associating the labelled conjugate with the first negative marker comprises a binding reagent, that binds an epitope of the first negative marker.

5. The assay device of claim 1 wherein the means for associating the labelled conjugate with the analyte and the means for associating the labelled conjugate with a first negative marker are identical.

6. The assay device of claim 1, wherein the one or more capture zones comprises an immobilised capture species that binds the first negative marker.

7. The assay device of claim 1, wherein the immobilised capture species in a capture zone binds an epitope of the first negative marker that is not present on the analyte.

8. The assay device of claim 1, wherein the reagent zone comprises a mobilisable first negative marker binding reagent that is specific for the first negative marker, linked to a first binding partner and the capture zone comprises an immobilised second binding partner for the first binding partner.

9. The assay device of claim 1, wherein at least one capture zone comprises a first line or region of immobilised capture species, and one or more additional lines or regions of immobilised capture species located downstream of the first line or region of immobilised capture species.

10. The assay device of claim 1, wherein the detection zone comprises an immobilised binding reagent that binds the analyte.

11. The assay device of claim 1, wherein the immobilised binding reagent in the detection zone does not bind a negative marker and/or binds an epitope of the analyte that is not present in the first negative marker.

12. The assay device of claim 1, wherein the reagent zone comprises a mobilisable binding reagent that binds the analyte, linked to a first binding partner and the detection zone comprises an immobilised second binding partner for the first binding partner.

13. The assay device of claim 1, wherein the analyte is indicative of the presence of a first condition and the first negative marker is indicative of the absence of the first condition, and wherein the first condition is pregnancy.

14. The assay device of claim 1, wherein the first negative marker and the analyte share a common epitope.

15. The assay device of claim 1, wherein the first negative marker and the analyte share a common structural feature.

16. The assay device of claim 1, wherein the analyte is hCG and/or wherein the first negative marker is FSH.

17. The assay device of claim 1, wherein the mobilisable labelled conjugate comprises an anti-alpha hCG antibody.

18. The assay device of claim 1, wherein the one or more capture zones comprises an anti-beta FSH antibody.

19. The assay device of claim 1, wherein the detection zone comprises an anti-beta hCG antibody.

20. The assay device of claim 1, wherein the detectable label comprises a colloidal metallic particle or latex.

21. The assay device of claim 1, adapted to reduce the quantity of labelled conjugate that reaches the detection zone in the presence of one or more additional negative markers.

22. The assay device of claim 1, wherein capture of the complex is achieved by a specific binding reaction with the analyte.

23. The assay device of claim 1, the means for associating the labelled conjugate with the analyte and the means for associating the labelled conjugate with a first negative marker are different.

24. The assay device of claim 1, wherein the immobilised binding reagent in the detection zone comprises an antibody.

25. The assay device of claim 15, wherein the common structural feature comprises a subunit of the analyte.

* * * * *